(12) United States Patent
Nikolich-Zugich et al.

(10) Patent No.: US 10,882,903 B2
(45) Date of Patent: Jan. 5, 2021

(54) METHODS AND COMPOSITIONS FOR TREATING AN ALPHAVIRUS INFECTION

(71) Applicant: ARIZONA BOARD OF REGENTS ON BEHALF OF THE UNIVERSITY OF ARIZONA, Tucson, AZ (US)

(72) Inventors: Janko Nikolich-Zugich, Tucson, AZ (US); Jennifer Uhrlaub, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 15/574,351

(22) PCT Filed: May 18, 2016

(86) PCT No.: PCT/US2016/033093
§ 371 (c)(1),
(2) Date: Nov. 15, 2017

(87) PCT Pub. No.: WO2016/187312
PCT Pub. Date: Nov. 24, 2016

(65) Prior Publication Data
US 2018/0134778 A1 May 17, 2018

Related U.S. Application Data

(60) Provisional application No. 62/163,199, filed on May 18, 2015.

(51) Int. Cl.
| C07K 16/22 | (2006.01) |
| A61K 39/12 | (2006.01) |
| A61P 31/14 | (2006.01) |
| A61K 39/395 | (2006.01) |
| A61K 45/06 | (2006.01) |
| A61K 39/00 | (2006.01) |

(52) U.S. Cl.
CPC ............ *C07K 16/22* (2013.01); *A61K 39/12* (2013.01); *A61K 39/3955* (2013.01); *A61K 45/06* (2013.01); *A61P 31/14* (2018.01); *A61K 2039/505* (2013.01); *A61K 2039/58* (2013.01); *C07K 2317/21* (2013.01); *C07K 2317/24* (2013.01); *C07K 2317/55* (2013.01); *C07K 2317/56* (2013.01); *C07K 2317/622* (2013.01); *C07K 2317/76* (2013.01); *C12N 2770/36111* (2013.01)

(58) Field of Classification Search
CPC .................. C07K 16/22; C12N 2770/36111
See application file for complete search history.

(56) References Cited

U.S. PATENT DOCUMENTS

| 5,520,926 A | 5/1996 | Ferguson |
| 5,571,714 A | 11/1996 | Dasch |
| 5,583,103 A | 12/1996 | Ruoslahti |
| 5,654,270 A | 8/1997 | Ruoslahti |
| 5,683,988 A | 11/1997 | Chung |
| 5,693,607 A | 12/1997 | Segarini |
| 5,693,610 A | 12/1997 | Matsunaga |
| 5,705,609 A | 1/1998 | Ruoslahti |
| 5,726,149 A | 3/1998 | Ruoslahti |
| 5,772,995 A | 6/1998 | Fakhrai |
| 5,807,708 A | 9/1998 | Falb |
| 5,821,234 A | 10/1998 | Dzau |
| 5,824,655 A | 10/1998 | Border |
| 5,830,847 A | 11/1998 | Letarte |
| 5,834,248 A | 11/1998 | Falb |
| 5,869,462 A | 2/1999 | Dzau |
| 5,948,639 A | 9/1999 | Gimeno |
| 5,958,411 A | 9/1999 | Logan |
| 6,001,969 A | 12/1999 | Lin |
| 6,008,011 A | 12/1999 | Lin |
| 6,010,872 A | 1/2000 | Lin |
| 6,015,693 A | 1/2000 | Letarte |
| 2009/0004182 A1* | 1/2009 | Baiocchi ............... A61P 35/02 424/133.1 |
| 2013/0295115 A1* | 11/2013 | Cherry ................... A61K 33/26 424/172.1 |

FOREIGN PATENT DOCUMENTS

| EP | 813875 | 12/1997 |
| EP | 874046 | 10/1998 |
| JP | 8119984 | 5/1996 |
| WO | WO 91/04748 | 4/1991 |
| WO | WO 91/08291 | 6/1991 |
| WO | WO 92/00330 | 1/1992 |
| WO | WO 93/09228 | 5/1993 |
| WO | WO 93/09800 | 5/1993 |
| WO | WO 93/10808 | 6/1993 |
| WO | WO 94/09812 | 5/1994 |
| WO | WO 94/10187 | 5/1994 |
| WO | WO 94/25588 | 11/1994 |
| WO | WO 95/10610 | 4/1995 |
| WO | WO 97/00691 | 1/1997 |
| WO | WO 97/13844 | 4/1997 |
| WO | WO 97/31020 | 8/1997 |
| WO | WO 97/38729 | 10/1997 |
| WO | WO 97/40848 | 11/1997 |
| WO | WO 98/03663 | 1/1998 |
| WO | WO 98/07735 | 2/1998 |

(Continued)

OTHER PUBLICATIONS

Weaver, S. C., et al., 2012, Chikungunya virus and prospects fora vaccine, Exp. Rev. Vacc. 11(9):1087-1101.*

(Continued)

*Primary Examiner* — Jeffrey S Parkin

(74) *Attorney, Agent, or Firm* — Casimir Jones, S.C.; Tanya A. Arenson

(57) ABSTRACT

Methods and pharmaceutical compositions for preventing, treating or suppressing symptoms of a disorder associated with an alphavirus infection. In particular, the present invention relates to preventing, treating or suppressing symptoms of a disorder associated with an alphavirus infection through inhibiting the activity and/or expression of Transforming Growth Factor Beta (TGF-β) in a subject suffering from or at risk for suffering from an alphavirus infection.

6 Claims, 12 Drawing Sheets

(56) References Cited

FOREIGN PATENT DOCUMENTS

Figure 1:
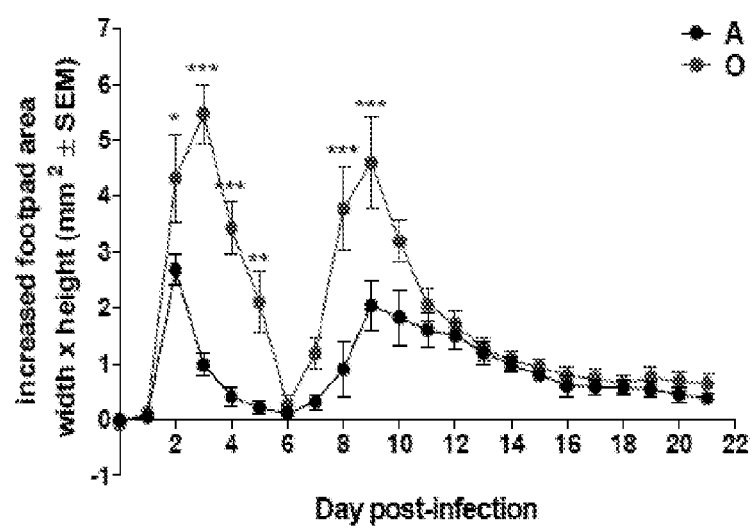

| | | |
|---|---|---|
| WO | WO 98/07849 | 2/1998 |
| WO | WO 98/08529 | 3/1998 |
| WO | WO 98/17304 | 4/1998 |
| WO | WO 98/45467 | 10/1998 |
| WO | WO 98/48024 | 10/1998 |
| WO | WO 98/53068 | 11/1998 |
| WO | WO 98/53830 | 12/1998 |
| WO | WO 98/55512 | 12/1998 |
| WO | WO 98/56913 | 12/1998 |
| WO | WO 99/50296 | 10/1999 |
| WO | WO 00/66631 | 11/2000 |

OTHER PUBLICATIONS

Singh, P., et al., 2013, Current research and clinical trials for a vaccine against Chikungunya virus, Vaccine: Development and Therapy 3:35-46.*
Winkler, K., et al., 2000, Changing the antigen binding specificity by single point mutations of an anti-p24 (HIV-1) antibody, J. Immunol. 165:4505-4514.*
Sela-Culang, I., et al., 2013, The structural basis of antibody-antigen recognition, Front. Immunol. 4:article 302, 1-13.*
Liu, Z., et al., 1999, Fine mapping of the antigen-antibody interaction of scFv215, a recombinant antibody inhibiting RNA polymerase II from *Drosophila* melanogaster, J. Mol. Recog. 12:103-111.*
Chatellier, J., et al., 1996, Functional mapping of conserved residues located at the VL and VH domain interface of a Fab, J. Mol. Biol. 264:1-6.*
Saxena, T., et al., Nov. 2013, Combined miRNA and mRNA signature identifies key molecular players and pathways involved in Chikunugunya virus infection in human cells, PLOS One 8(11):e79886 (pp. 1-11).*
Borgherini, G., et al., 2008 Clinical infectious diseases : an official publication of the Infectious Diseases Society of America 47:469-475.
Borgherini, G., P. et al., 2007 Clinical infectious diseases : an official publication of the Infectious Diseases Society of America 44:1401-1407.
Burt, F.J., et al., "Chikungunya: a re-emerging virus." Lancet 379:662-671.
Chaaitanya, I.K., et al.., of proinflammatory cytokines and chemokines in chronic arthropathy in CHIKV infection. 2011 Viral immunology 24:265-271.
Chow, A., et al., Persistent Arthralgia Induced by Chikungunya Virus Infection is Associated with Interleukin-6 and Granulocyte Macrophage Colony-Stimulating Factor 2011 The Journal of infectious diseases 203:149-157.
Couderc, T., et al., A Mouse Model for Chikungunya: Young Age and Inefficient Type-I Interferon Signaling Are Risk Factors for Severe Disease 2008 PLoS pathogens 4:e29.
Crowson, C.S., et al., The lifetime risk of adult-onset rheumatoid arthritis and other inflammatory autoimmune rheumatic diseases. 2011 Arthritis and rheumatism 63:633-639.
Das, T., et al.., Chikungunya fever: CNS infection and pathologies of a re-emerging arbovirus 2010 Progress in neurobiology 91:121-129.
Decman, V., et al., Defective CD8 T Cell Responses . . . 2012 Journal of immunology (Baltimore, Md. : 1950) 188:1933-1941.
Dupuis-Maguiraga, L., et al., Chikungunya Disease: Infection-Associated Markers from the Acute to the Chronic Phase of Arbovirus-Induced Arthralgia PLoS neglected tropical diseases 6:e1446.
Fischer, M., and J.E. Staples. "Notes from the Field: Chikungunya Virus Spreads in the Americas—Caribbean and South America, 2013-2014" 2014 Morbidity and mortality weekly report 63:500-501.
Gardner, C.L., et al., Interferon-alpha/beta deficiency greatly exacerbates arthritogenic disease in mice infected with wild-type chikungunya virus but not with the cell culture-adapted live-attenuated 181/25 vaccine candidate. Virology. 2012. 425:103-112.
Gardner, J., et al., "Chikungunya Virus Arthritis in Adult Wild-Type Mice" 2010 Journal of virology 84:8021-8032.
Gubler "The global emergence/resurgence of arboviral diseases as public health problems." (2002) Arch. Med. Res. 33:330-42.
Hawman, D.W., et al., "Chronic joint disease caused by persistent Chikungunya virus infection is controlled by the adaptive immune response." 2013 Journal of virology 87:13878-13888.
Her, Z., et al., "Chikungunya: a bending reality" 2009 Microbes and infection / Institut Pasteur 11:1165-1176.
Hoarau, J.J., et al., 2010 Journal of immunology (Baltimore, Md.: 1950) 184:5914-5927.
International Search Report, International Patent Application No. PCT/US2016/033093, dated Aug. 25, 2016, 8 pages.
Isaka et al., "Gene therapy by transforming growth factor-β receptor-IgG Fc chimera suppressed extracellular matrix accumulation in experimental glomerulonephritis" 1999, Kidney Int., 55:465-475.
Kekow, J. et al. "Transforming growth factor f8 and noncytopathic mechanisms of immunodeficiency in human immunodeficiency virus infection" Proc. Nat'l. Acad. Sci. vol. 87, pp. 8321-8325, Nov. 1990.
Kelvin A.A., et al., Inflammatory cytokine expression is associated with chikungunya virus resolution and symptom severity. 2011 PLoS neglected tropical diseases 5:e1279.
Kularatne, S.A., et al., Epidemiology, Clinical Manifestations, and Long-Term Outcomes of a Major Outbreak of Chikungunya in a Hamlet in Sri Lanka, in 2007: A Longitudinal Cohort Study. 2012 Journal of tropical medicine 2012:639178.
Kumar S., et al., Mouse macrophage innate immune response to chikungunya virus infection. 2012 Virology journal 9:313.
Lenferink, A E, et al., Expression of TGF-beta type II receptor antisense RNA impairs TGF-beta signaling in vitro and promotes mammary gland differentiation in vivo. Int J. Cancer. Dec. 20, 2003; 107(6):919-28.
McIntyre, T.M., et al., Transforming Growth Factor Beta1 Selectivity Stimulates Immunoglobulin G2b Secretion by Lipopolysaccharide-activated Murine B Cells.1993 The Journal of experimental medicine 177:1031-1037.
Messaoudi, I., et al., Chikungunya virus infection results in higher and persistent viral replication in aged rhesus macaques due to defects in anti-viral immunity. 2013 PLoS neglected tropical diseases 7:e2343.
Moro, et al., Long-term chikungunya infection clinical manifestations after an outbreak in Italy: A prognostic cohort study. 2012 The Journal of infection 65:165-172.
Ng, L.F., et al., IL-1beta, IL-6, and RANTES as biomarkers of Chikungunya severity. 2009 PloS one 4:e4261.
Pal, P., et al., Development of a Highly Protective Combination Monoclonal Antibody Therapy against Chikungunya Virus. 2013 PLoS pathogens 9:e1003312.
Powers, A.M., and C.H. Logue. Changing patterns of chikungunya virus: re-emergence of a zoonotic arbovirus. 2007, The Journal of general virology 88:2363-2377.
Robinson, M.C. An Epidemic of Virus Disease in Southern Province, Tanganyika Territory, In 1952-1953. 1955 Transactions of the Royal Society of Tropical Medicine and Hygiene 49:28-32.
Rudd, B.D., et al., Nonrandom attrition of the naive CD8+ T-cell pool with aging governed by T-cell receptor:pMHC interactions. 2011 Proceedings of the National Academy of Sciences of the United States of America 108:13694-13699.
Sidwell et al. Viruses and the Bunya—and Togaviridae families: potential as bioterrorism agents and means of control. (2003) Antiviral Res. 57:101-11.
Souza et al., 1999, Novel Cloning Method for Recombinant Adenovirus Construction in *Escherichia coli*. Biotechniques, 26:502-508.
Stroschein, et al., Negative feedback regulation of TGF-beta signaling by the SnoN oncoprotein. 1999, Science 286:771-774.
Teo, T.H., et al., A Pathogenic Role for CD4+ T Cells during Chikungunya Virus Infection in Mice. 2013 Journal of immunology (Baltimore, Md. : 1950) 190:259-269.

(56) References Cited

OTHER PUBLICATIONS

Vogel, A New Blocker for the TGF-Beta Pathway. 1999, Science 286:665.

Wahl, S.M., et al., Reversal of acute and chronic synovial inflammation by anti-transforming growth factor beta. 1993 The Journal of experimental medicine 177:225-230.

Werner, C. 2011. The Older Population: 2010 Census Briefs, Nov. 2011, pp. 1-19.

Zhao, et al, Epithelium-specific adenoviral transfer of a dominant-negative mutant TGF-beta type II receptor stimulates embryonic lung branching morphogenesis in culture and potentiates EGF and PDGF-AA. 1998, Mech. Dev., 72:89-100.

Zhao, et al., Adenovirus-mediated decorin gene transfer prevents TGF-β-induced inhibition of lung morphogenesis. 1999, Am. J. Physiol., 277:L412-L422.

\* cited by examiner

METHODS AND COMPOSITIONS FOR TREATING AN ALPHAVIRUS INFECTION

CROSS REFERENCE TO RELATED APPLICATIONS

This application is a Section 371 U.S. national stage entry of International Patent Application No. PCT/US2016/033093, International Filing Date May 18, 2016, which claims the benefit of U.S. Provisional Application Ser. No. 62/163,199, filed May 18, 2015, which are incorporated herein by reference in their entireties.

FIELD OF THE INVENTION

Methods and pharmaceutical compositions for preventing, treating or suppressing symptoms of a disorder associated with an alphavirus infection. In particular, the present invention relates to preventing, treating or suppressing symptoms of a disorder associated with an alphavirus infection through inhibiting the activity and/or expression of Transforming Growth Factor Beta (TGF-$\beta$) in a subject suffering from or at risk for suffering from an alphavirus infection.

INTRODUCTION

There are many alphaviruses distributed around the world with the ability to cause human disease. Infectious arthritis, encephalitis, rashes, and fever are the most commonly observed symptoms. Larger mammals such as humans and horses are usually dead-end hosts or play a minor role in viral transmission; however, in the case of Venezuelan equine encephalitis the virus is mainly amplified in horses. In most other cases the virus is maintained in nature in mosquitoes, rodents and birds.

Alphavirus infections are spread by insect vectors such as mosquitoes. Once a human is bitten by the infected mosquito, the virus can gain entry into the bloodstream, causing viremia. The alphavirus can also get into the CNS where it is able to grow and multiply within the neurones. This can lead to encephalitis, which can be fatal.

There are currently no specific treatments or proven cures for alphavirus infections such that reliance on host immunity responses is the standard course of care. Moreover, no FDA-approved anti-alphaviral vaccines exist. Accordingly, there is a great need in the art for effective methods for treating alphaviral infections.

SUMMARY OF THE INVENTION

Viruses of the genus Alphaviridae belong to the group IV Togaviridae family of viruses based on the well-known Baltimore taxonomic classification of viruses. Of the roughly 30 known alphaviruses, at least one third cause significant diseases in humans and animals worldwide, which manifest with such debilitating symptoms as encephalitis, arthritis, rashes, fevers, headache, nausea, myalgia, arthralgia (joint pain), arthropathy (diseases of the joint), chills, diarrhea, vomiting, lymphadenitis, malaise, and muscle soreness. In particular, Sindbis, Semliki Forest, O'nyong'nyong, Chikungunya, Mayaro, Ross River, Barmah Forest, Eastern Equine Encephalitis, Western Equine Encephalitis, and Venezuelan Equine Encephalitis viruses are medically relevant alphaviruses that generally infect human populations via insect vectors (e.g., mosquitoes) and can cause fatal encephalitis if alphaviral infection reaches the central nervous system (CNS). Neurotropic alphaviruses are also important members of the growing list of emerging or resurging public health threats (see, e.g., Gubler (2002) Arch. Med. Res. 33:330-42) and are listed as CDC and NIAID category B bioterrorism agents due in part to numerous characteristics that make them potential biological weapons: (i) high clinical morbidity and mortality; (ii) potential for aerosol transmission; (iii) lack of effective countermeasures for disease prevention or control; (iv) public anxiety elicited by CNS infections; (v) ease with which large volumes of infectious materials can be produced; and (vi) potential for malicious introduction of foreign genes designed to increase alphavirus virulence (see, e.g., Sidwell et al. (2003) Antiviral Res. 57:101-11).

Chikungunya virus (CHIKV) is a mosquito-borne Alphavirus endemic to Africa and Asia, which causes sudden onset of fever, rash, and debilitating poly-arthralgia in peripheral joints that can persist for years, particularly in older individuals. In 2013, CHIKV spread to the western hemisphere resulting in more than one million cases. Autochthonous transmission in the United States was confirmed in 2014. In response to the increased geographic distribution of CHIKV and the likelihood that elderly immune-naïve populations may experience severe and life-threatening disease, a mouse model of age-related vulnerability to CHIKV infection was developed. Experiments conducted during the course of developing embodiments for the present invention demonstrated reduced ability of old mice to mount effective immune responses to CHIKV and control viremia, leading to increased disease severity and viral persistence in the joints. It was shown that ineffective immune responses were due, in part, to uncoordinated cytokine production. Specifically, CXCL9 and TGF-$\beta$, were identified as key contributors to impaired CD4 and antibody responses against viral epitopes in old mice. Moreover, neutralization of TGF-$\beta$ reduced acute joint swelling, restored Ab responses, and virtually eliminated chronic joint pathology.

Accordingly, the present invention provides methods and pharmaceutical compositions for preventing, treating or suppressing symptoms of a disorder associated with an alphavirus infection. In particular, the present invention relates to preventing, treating or suppressing symptoms of a disorder associated with an alphavirus infection through inhibiting the activity and/or expression of TGF-$\beta$ in a subject suffering from or at risk for suffering from an alphavirus infection.

In certain embodiments, the present invention provides methods for treating an alphavirus infection in a subject, comprising administering to the subject an effective amount of an agent that inhibits one or more functions of TGF-$\beta$. In some embodiments, the alphavirus is selected from the group consisting of Aura virus, Babanki, Barmah Forest virus, Bebaru virus, Buggy Creek, Cabassou virus, Chikungunya virus, Eastern equine encephalitis virus, Everglades virus, Fort Morgan virus, Getah virus, Highlands J virus, Kyzylagach virus, Mayaro virus, Middelburg virus, Mosso das Pedras virus, Mucambo virus, Ndumu virus, O'nyong-nyong virus, Pixuna virus, Rio Negro virus, Ross River virus, Sagiyama virus, Salmon pancreas disease virus, Semliki Forest virus, Sindbis virus, Southern elephant seal virus, Tonate virus, Trocara virus, Una virus, Venezuelan equine encephalitis virus, Western equine encephalitis virus, and Whataroa virus.

Such methods are not limited to a particular type of TGF-$\beta$ inhibitor. For example, in some embodiments, the TGF-$\beta$ inhibitor is an anti-TGF-$\beta$ antibody, a TGF-$\beta$ antisense molecule, a vector encoding a TGF-$\beta$ antisense molecule, a silencing RNA which silences TGF-β, a TGF-β receptor anti-sense molecule, a vector encoding a TGF-β receptor antisense molecule, and a silencing RNA which silences TGF-β receptors.

In some embodiments, inhibition of one or more functions of TGF-β through administration of the TGF-β inhibitor results in a decrease in symptoms related to the alphaviral infection. For example, in some embodiments, such symptoms include, but are not limited to, encephalitis, arthritis, rashes, fevers, headache, nausea, myalgia, arthralgia, arthropathy, chills, diarrhea, vomiting, lymphadenitis, malaise, and muscle soreness.

In some embodiments, the methods described herein further comprise administering to the subject an effective amount of at least one additional therapeutic agent (e.g., an agent that reduces alphaviral replication, reduces the time to alphaviral clearance, reduces morbidity or mortality in the clinical course of the alphaviral infection, reduces subject symptoms caused by the alphaviral infection, or reduces potential side effects of the TGF-β inhibitor). In some embodiments, the at least one additional therapeutic agent is selected from the group consisting of a nucleoside analog, mycophenolic acid, inhibitors of inosine monophosphate dehydrogenase (IMPDH), anti-alphaviral neutralizing monoclonal antibodies, poly ICLC, triaryl pyrazolin, anti-alphaviral ribozymes, zinc-finger antiviral protein, lactoferrin, and anti-alphaviral antisense RNA inhibitors.

In some embodiments of the methods described herein, the TGF-β inhibitor and the at least one additional therapeutic agent are administered together as part of a single composition or administered separately. In some embodiments, the administering step comprises administering the agent to the central nervous system. In some embodiments of the methods described herein, the subject is a human.

BRIEF DESCRIPTION OF DRAWINGS

FIG. 1: Age increases acute CHIKV-induced joint swelling. A (12 weeks) and O (18-20 months) C57BL/6 mice were inoculated via footpad (f.p.) route with 1000 pfu of CHIKV. The width and height of the inoculated foot was measured daily through day 21 post-infection. Increased footpad area on each day post-infection was calculated by multiplying the width and height of the foot and subtracting day 0 area for each mouse. Data are representative of three independent experiments of 10-16 mice per group. Two-way ANOVA ($P<0.001$) with Bonferroni post-test *, $P<0.05$; , $P<0.01$; *, $P<0.001$.

FIG. 2A-D. Prolonged CHIKV viremia with age leads to persistent infection. Infection was as in FIG. 1A. Serum, non-inoculated control (CTRL) and CHIKV-inoculated (CHIKV) feet were harvested on indicated days post-infection and assayed for viral titer by plaque assay (A-C: data are representative of three independent experiments of 7-8 mice per group) or quantitative PCR for viral genome copies (D: data are representative of two independent experiments of 16-18 mice per group). (A) Serum viral titers on days 1-4 post-infection when virus is cleared in the blood. (B) Viral titers in CTRL and CHIKV feet on day 3 post-infection. (C) Viral titers in CTRL and CHIKV feet on day 9 post-infection. (D) Genome copies of virus in CHIKV feet on day 60 post-infection. Data was log-transformed and statistical significance indicated on the graphs was evaluated by unpaired Student's t-test. Horizontal lines indicate the median.

FIG. 3A-D. Age-related impairment of innate immune cell subsets in lymph node. Infection was as in FIG. 1A. Popliteal LNs were collected from either naïve or CHIKV-infected A and O mice at day 3, 7, or 9 post-infection. The LN draining from the CHIKV-inoculated foot is indicated as dLN and from the non-inoculated foot as ndLN. (A) Representative LNs from naïve and day 3 CHIKV infected A and O mice. O mice have visibly smaller LNs as compared to A both when naïve and after CHIKV infection. Absolute number of (B) dendritic cells, (C) macrophages, and (D) NK cells as determined by FCM per gating strategy in FIG. 10. Tables under graphs B-D indicate the average fold-increase from naïve for each age in either the dLN or ndLN. Data are representative of three independent experiments of 7-8 mice per group. Statistical significance indicated on the graphs and tables was evaluated by unpaired Student's t-test *, $P<0.05$; , $P<0.01$; *, $P<0.001$.

FIG. 4A-E. O LN fails to recruit sufficient T and B cell numbers during CHIKV infection. Infection was as in FIG. 1A. Popliteal LNs were collected from either naïve or CHIKV-infected A and O mice at day 3, 7, or 9 post-infection. The LN draining from the CHIKV-inoculated foot is indicated as dLN and from the non-inoculated foot as ndLN. Absolute number of (A) CD4 T cells, (B) CD8 T cells, and (C) B cells as determined by FCM per gating strategy in FIG. 9. Tables under graphs A-C indicate the average fold-increase from naïve for each age in either the dLN or ndLN. Splenocytes from CHIKV A and O mice were isolated on day 7 post-infection and stimulated for 6 hours in the presence of brefeldin A with overlapping peptide pools from the 9 indicated CHIKV proteins. IFNγ production by CD4 T cells (D) and CD8 T cells (E) is expressed as the frequency of the total population. Data are representative of at least three independent experiments of 7-8 mice per group. Statistical significance indicated on the graphs and tables was evaluated by unpaired Student's t-test *, $P<0.05$; , $P<0.01$; *, $P<0.001$.

FIG. 5A-F. Quantitative and functional impairment of the CHIKV-specific antibody response with age. Infection was as in FIG. 1A. Serum was collected from A and O mice at the indicated time points and the amount of CHIKV-specific IgM (A), total IgG (B), IgG2b (C), IgG2c (D), and IgG1 (E) was determined by ELISA. (F) Plaque reduction neutralizing antibody titers (PRNT) were determined at day 9 and 60 post-infection. Data shown are from one representative assay run on samples from multiple experiments. Each assay was done at least twice with n=4-24 per group. Statistical significance indicated on the graphs and tables was evaluated by unpaired Student's t-test *, $P<0.05$; , $P<0.01$; *, $P<0.001$.

FIG. 6A-B. Dysregulated cytokine production in aged CHIKV-infected mice. Infection was as in FIG. 1. Serum was collected from A and O mice and assayed by ELISA for (A) CXCL9 or (B) TGF-β concentration at days 2 or 9 post-infection, respectively. Data are representative of two independent assays run on samples collected from two independent animal experiments of 7-8 mice per infection group and 3 naïve mice of each age. Statistical significance indicated on the graphs and tables was evaluated by unpaired Student's t-test *, $P<0.05$; , $P<0.01$; *, $P<0.001$.

FIG. 7A-C. Blocking TGF-β prevents CHIKV-induced disease and restores neutralizing antibody titers in old mice. A and O C57BL/6 mice were treated with 100 ug of anti-TGF-β antibody or isotype control by f.p. route in the CHIKV-inoculated foot on days −1, 1, 3, and 5 of CHIKV-infection. CHIKV infection was as in FIG. 1A. (A) The width and height of the inoculated foot was measured daily through day 15 post-infection. Increased footpad area on each day post-infection was calculated by multiplying the width and height of the foot and subtracting day 0 area for each mouse. Data are representative of three independent experiments of 8 mice per group. Two-way ANOVA between each age of treated or untreated mice (P<0.001) with Bonferroni post-test *, P<0.05; , P<0.01; *, P<0.001. (B) Blinded H&E stained histology sections were evaluated by an anatomic pathologist for arthritis and metatarsal muscle Inflammation (MMI). 1/6 untreated A; 5/6 treated A; 4/6 untreated 0; and 2/6 treated 0 scored as having Arthritis and/or MMI at day 90 post-infection. (C) Plaque reduction neutralizing antibody titers (PRNT) were determined at day 90 post-infection. Data shown are from one representative assay run on samples from multiple experiments. Each assay was done at least twice with n=11-12 per group. Statistical significance indicated on the graphs was evaluated by unpaired Student's t-test , P<0.01; *, P<0.001.

Figure 8:
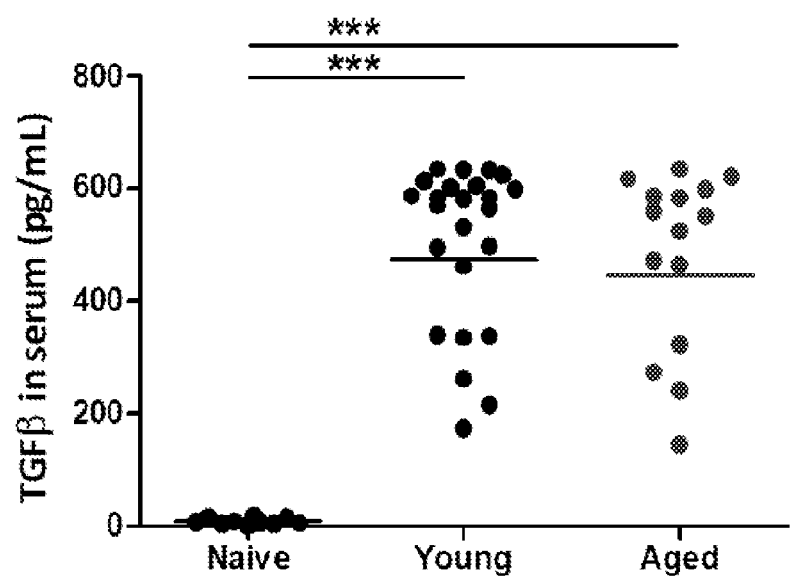

FIG. 8. shows TGF-β levels in human beings suffering from CHIKV.

Figure 9:
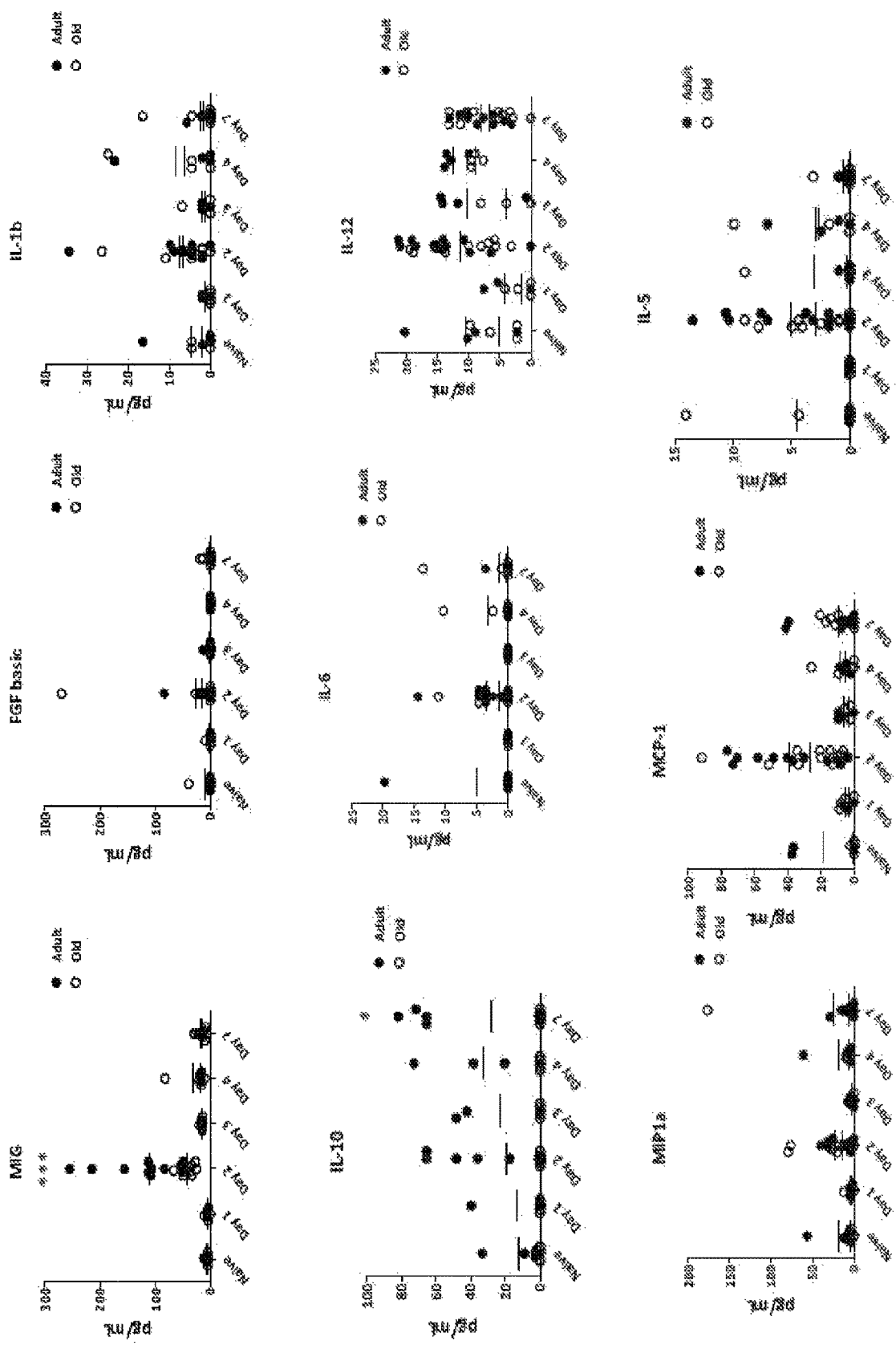
Figure 9:
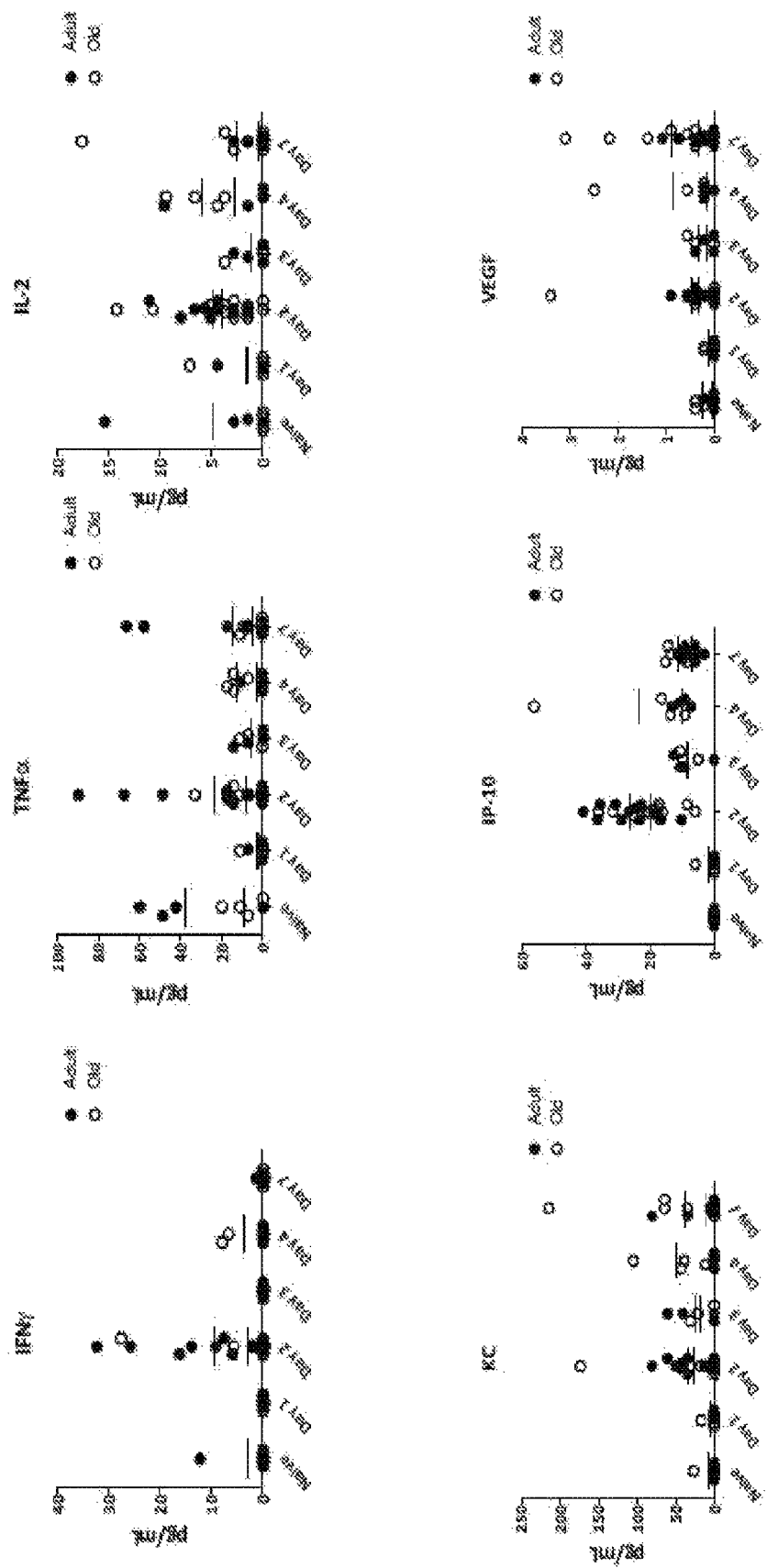

FIG. 9. Cytokine array data (see, Example V).

Figure 10A:
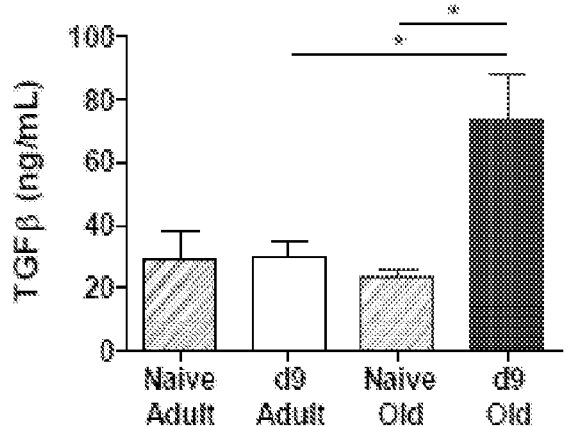
Figure 10B:
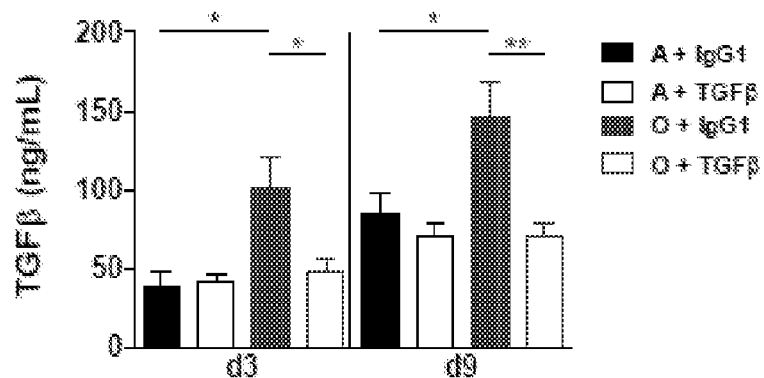
Figure 10C:
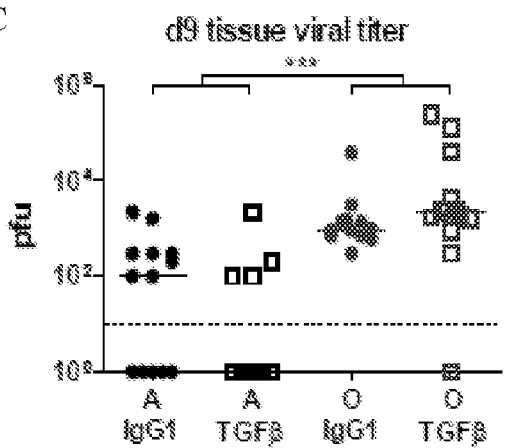

FIG. 10A-C. (A) A and O C57BL/6 mice were inoculated via subcutaneous (s.c.) route with 1000 pfu of WNV 385-99. Naïve and infected mice were bled for serum on day 10 post-infection and assayed by ELISA for TGF-β concentration. Data are representative two independent assays run on samples collected from two independent animal experiments of 7-10 mice per group. Statistical significance indicated on the graphs was evaluated by unpaired Student's t-test *, P<0.05; **, P<0.01. (B) A and O C57BL/6 mice were either untreated or treated with 100 ug of anti-TGF-β antibody by f. p. route in the CHIKV-inoculated foot on days −1, 1, 3, and 5 of CHIKV-infection. CHIKV infection was as in FIG. 1A. Mice were bled for serum on days 3 and 9 post-infection and assayed by ELISA for TGF-β concentration. Data are representative two independent assays run on samples collected from two independent animal experiments of 6-13 mice per group. Statistical significance indicated on the graphs was evaluated by unpaired Student's t-test *, P<0.05; , P<0.01. (C) Infection and treatment was as in FIG. 7A. CHIKV-inoculated (CHIKV) feet were harvested on day 9 post-infection and assayed for viral titer by plaque assay. Data represented include viral titers from two independent animal experiments of 7-8 mice per group. Statistical significance indicated on the graphs was evaluated by unpaired Student's t-test *, P<0.001.

DEFINITIONS

In order that the present invention may be more readily understood, certain terms are first defined. Additional definitions are set forth throughout the detailed description.

The term "alphavirus," and its grammatical variants, refers to a group of Togaviridae (Group IV) family of viruses characterized by one or more of the following: (i) a positive sense, single-stranded RNA genome; (ii) RNA that is 5' capped and 3'-polyadenylated; (iii) viral particles that are enveloped, have a 70 nm diameter, and have a 40 nm isometric nucleocapsid; (iv) viral replication in the cytoplasm of host cells; (v) lack a DNA phase during the viral replication cycle; and (vi) maintain virions that mature by budding through the plasma membrane. A non-limiting list of exemplary alphaviruses includes Aura virus (AURA), Babanki (BAB), Barmah Forest virus (BF), Bebaru virus (BEB), Buggy Creek, Cabassou virus (CAB), Chikungunya virus (CHIK), Eastern equine encephalitis virus (EEE), Everglades virus (EVE), Fort Morgan virus (FM), Getah virus (GET), Highlands J virus (HJ), Kyzylagach virus (KYZ), Mayaro virus (MAY), Middelburg virus (MID), Mosso das Pedras virus (78V3531), Mucambo virus (MUC), Ndumu virus (NDU), O'nyong-nyong virus (ONN), Pixuna virus (PIX), Rio Negro virus (AG80), Ross River virus (RR), Sagiyama virus (SAG), Salmon pancreas disease virus (SPDV), Semliki Forest virus (SF), Sindbis virus (SIN), Southern elephant seal virus, Tonate virus, Trocara virus, Una virus (UNA), Venezuelan equine encephalitis virus (VEE), Western equine encephalitis virus (WEE), and Whataroa virus (WHA). Sindbis, Semliki Forest, O'nyong'nyong, Chikungunya, Mayaro, Ross River, Barmah Forest, Eastern Equine Encephalitis, Western Equine Encephalitis, and Venezuelan Equine Encephalitis viruses are particularly relevant for medical intervention in humans. Alphaviruses are evolutionarily differentiated based on nucleotide sequence of the nonstructural proteins, of which there are four (nsP1, nsP2, nsP3 and nsP4). The genus segregates into New World (American) and Old World (Eurasian/African/Australasian) alphaviruses based on geographic distribution. It is estimated that New World and Old World viruses diverged between 2,000 and 3,000 years ago (see, e.g., Harley et al. (2001) Clin. Microbiol. Rev. 14:909-932). Among the alphavirus species, there are at least seven distinct serocomplexes (SF, EEE, MID, NDU, VEE, WEE and BFV) into which members of the genus are sub-divided (see, e.g., Khan et al. (2002) J. Gen. Virol. 83:3075-3084 and Harley et al. (2001) Clin. Microbiol. Rev. 14:909-932). Based on genomic sequence data from six of the seven serocomplexes, alphaviruses have been grouped into three large groups VEE/EEE, SFV and SIN. The VEE-EEE group is exclusively made up of New World viruses with a distribution in North America, South America and Central America.

The term "biological sample" is intended to include tissues, cells and biological fluids isolated from a subject, as well as tissues, cells and fluids present within a subject.

The term "encephalitis" refers to an acute inflammation of the brain. Viral encephalitis can occur either as a direct effect of a viral infection or as one of the sequelae of a latent infection.

The terms "individual," "host," "subject," and "patient" are used interchangeably herein, and refer to a mammal, including, but not limited to, primates, including simians and humans.

The term "therapeutically effective amount" refers to an amount of a therapeutic agent, or a rate of delivery of a therapeutic agent, effective to facilitate a desired therapeutic effect. The precise desired therapeutic effect will vary according to the condition to be treated, the formulation to be administered, and a variety of other factors that are appreciated by those of ordinary skill in the art. In certain embodiments, the therapeutically effective amount of a TGF-β inhibitor in combination with a second therapeutic agent is an amount that is synergistic. As used herein, a "synergistic combination" or a "synergistic amount" of a TGF-β inhibitor and a second therapeutic agent is a combination or amount that is more effective in the therapeutic or prophylactic treatment of a disease than the incremental improvement in treatment outcome that could be predicted or expected from a merely additive combination of (i) the therapeutic or prophylactic benefit of the TGF-β inhibitor when administered at that same dosage as a monotherapy and (ii) the therapeutic or prophylactic benefit of the second therapeutic agent when administered at the same dosage as a monotherapy.

The terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease, such as in encephalitis resulting in the context of alphavirus infection; (b) inhibiting the disease (i.e., arresting its development); and (c) relieving the disease (i.e., causing regression of the disease).

TGF-β is a disulfide linked dimer that is synthesized as a preproprotein of about 400 amino acids (aa) which is cleaved prior to secretion to produce mature TGF-β. The N-terminal cleavage fragment, known as the "latency-associated peptide" (LAP), may remain noncovalently bound to the dimer, thereby inactivating TGF-β. TGF-β, isolated in vivo, is found predominantly in this inactive "latent" form associated with LAP. Latent TGF-β complex may be activated in several ways, for example, by binding to cell surface receptors called the cation-independent mannose-6-phosphate/insulin-like growth factor II receptor. Binding occurs through mannose-6-phosphate residues attached at glycosylation sites within LAP. Upon binding to the receptor, TGF-β is released in its mature form. Mature, active TGF-β is then free to bind to its receptor and exert its biological functions. The major TGF-β-binding domain in the type II TGF-β receptor has been mapped to a 19 amino acid sequence (see, e.g., Demetriou et al. (1996) J. Biol. Chem., 271:12755). As used herein, "TGF-β" refers to all isoforms of TGF-β. There are currently 5 known isoforms of TGF-β (1-5), all of which are homologous (60-80% identity) and all of which form homodimers of about 25 kD, and act upon common TGF-β cellular receptors (Types I, II, and III). The genetic and molecular biology of TGF-β is well known in the art (see, e.g., Roberts, 1998 Miner. Electrolyt and Metab. 24:111; Wrana, 1998, Miner. Electroly and Metab 24:120-130 and 174-180, WO 98/07849).

As used herein, a "TGF-β antagonist" or "TGF-β inhibitor" is any molecule that is able to decrease the amount or activity of TGF-β, either within a cell or within a physiological system. Preferably, the TGF-β inhibitor acts to decrease the amount or activity of a mammalian TGF-β1, 2, or 3. For example, a TGF-β inhibitor may be a molecule which inhibits expression of TGF-β at the level of transcription, translation, processing, or transport; it may affect the stability of TGF-β or conversion of the precursor molecule to the active, mature form; it may affect the ability of TGF-β to bind to one or more cellular receptors (e.g., Type I, II or III); or it may interfere with TGF-β signaling. The molecule may be, e.g., a peptide, a protein, an oligonucleotide, a nucleic acid, or a small chemical entity.

As used herein, a "pharmaceutically effective amount" is an amount effective to achieve the desired physiological result in a subject. Specifically, a pharmaceutically effective amount of a TGF-β inhibitor is an amount sufficient to decrease the quantity or activity of TGF-β for a period of time sufficient to reduce symptoms related to an alphavirus infection. The effective amount may vary depending on the specific TGF-β inhibitor selected, and is also dependent on a variety of factors and conditions related to the subject to be treated and the severity of the disorder (for example, the age, weight and health of the patient as well as dose response curves and toxicity data). The determination of a pharmaceutically effective amount for a given agent is well within the ability of those skilled in the art.

"Administration" to a patient is not limited to any particular delivery system and may include, without limitation, parenteral (including subcutaneous, intravenous, intramedullary, intraarticular, intramuscular, or intraperitoneal injection) rectal, topical, transdermal or oral (for example, in capsules, suspensions or tablets). Administration to a patient may occur in a single dose or in repeat administrations, and in any of a variety of physiologically acceptable salt forms, and/or with an acceptable pharmaceutical carrier and/or additive as part of a pharmaceutical composition. Once again, physiologically acceptable salt forms and standard pharmaceutical formulation techniques are well known to persons skilled in the art (see, for example, Remington's Pharmaceutical Sciences, Mack Publishing Co.). Administration of a TGF-β inhibitor to a host individual may also be by means of gene transfer, wherein a nucleic acid sequence encoding the antagonist is administered to the patient (host) in vivo or to cells in vitro, which are then introduced into the patient, and the inhibitor is thereafter produced by in situ expression of the product encoded by the nucleic acid sequence. Methods for gene therapy to deliver TGF-β antagonists are also well known to those of skill in the art (see, e.g., WO 96/25178).

DETAILED DESCRIPTION OF THE INVENTION

Chikungunya virus (CHIKV) is a re-emerging mosquito-borne Alphavirus endemic to India, Indian Ocean islands, and many other Asian and African countries including Indonesia, Singapore, Thailand, Malaysia, Sri Lanka, Congo, and Kenya (see, Powers, A. M., and C. H. Logue. 2007, The Journal of general virology 88:2363-2377). CHIKV typically causes a febrile illness with debilitating poly-arthralgia, fever and rash (see, Burt, F. J., et al., Lancet 379:662-671; Dupuis-Maguiraga, L., et al., PLoS neglected tropical diseases 6:e1446). In fact, it is from the distinctive severity of the joint pain and consequent protective position that Chikungunya disease was given its name—meaning "to become contorted" in the local language of Tanganyika part of today's Tanzania, where the disease was originally described in 1952 (see, Robinson, M. C. 1955 Transactions of the Royal Society of Tropical Medicine and Hygiene 49:28-32). During the more than 60 years since its discovery, CHIKV has widened its infection range via increased circulation, resulting in millions of people infected and higher incidences of complicated clinical manifestations (see, Her, Z., et al., 2009 Microbes and infection/Institut Pasteur 11:1165-1176). Whereas many patients resolve joint pain and swelling within 10-12 days, in a substantial proportion of cases symptoms persist much longer (see, Borgherini, G, et al., 2008 Clinical infectious diseases: an official publication of the Infectious Diseases Society of America 47:469-475). In a 2006 outbreak of CHIKV in Sri Lanka one study reported that of 512 infected patients 45% had chronic arthritic disability, which in 16% of subjects still persisted two years later (see, e.g., Kularatne, S. A., et al., 2012 Journal of tropical medicine 2012:639178). In 2013, CHIKV was reported in the Caribbean and South America with more than one million clinically diagnosed and 25,000 laboratory confirmed CHIKV cases (see, Fischer, M., and J. E. Staples. 2014 Morbidity and mortality weekly report 63:500-501).

During the initial phase of infection humans carry high viral titers (up to $10^{12}$ copies/mL of blood) capable of infecting local mosquito populations (see, Das, T., et al., 2010 Progress in neurobiology 91:121-129). Both species of mosquitoes that carry CHIKV are present in the U.S. (*Aedes* (Ae.) *albopictus* and Ae. *aegypti*), potentiating the possibility for the U.S. to become an endemic location. Indeed, Florida reported the first case of autochthonous transmission in the U.S.A in 2014. Further, the vast majority of the U.S. population is immunologically naïve to CHIKV, making it potentially susceptible to a higher incidence of severe disease as was seen after the arrival of CHIKV on the island of La Reunion in 2006 with >250,000 cases, accounting for almost 35% of the population, and 237 deaths (see, Borgherini, G., P. et al., 2007 Clinical infectious diseases: an official publication of the Infectious Diseases Society of America 44:1401-1407), the majority of which occurred in persons over the age of 75 (see, Josseran, L., et al., 2006 PLoS neglected tropical diseases 5:e1279). Indeed, age and rheumatic disease before infection have been identified as prime risk factors for persistent arthralgia lasting up to 5 years (see, Kularatne, S. A., et al., 2012 Journal of tropical medicine 2012:639178; Moro, et al., 2012 The Journal of infection 65:165-172). The United States has a rapidly aging population and a lifetime risk of inflammatory autoimmune rheumatic disease of 8.4% for women and 5.1% for men (see, Crowson, C. S., et al., 2011 Arthritis and rheumatism 63:633-639; Werner, C. 2011. The Older Population: 2010 Census Briefs). Taking into consideration all of these risk factors, the U.S. is vulnerable to epidemics of CHIKV that could have dramatic social and economic impact, particularly amongst the elderly.

The pathogenesis of CHIKV infection in humans has been studied mostly through clinical evaluations during and after disease outbreaks. Animal models have supplemented this data with critical insight to biological mechanisms required for the manifestation and resolution of CHIKV disease. Indeed, the number of publications devoted to CHIKV has increased dramatically since 2005 (see, Her, Z., et al., 2009 Microbes and infection/Institut Pasteur 11:1165-1176). Owing to the number and complexity of the studies done, the exact contribution of each facet of the immune response to disease presentation and resolution is subject to debate. The emerging consensus is that there is positive association between high levels of serum pro-inflammatory cytokines such as IFNαβ, IL-1β, IL-6, IL-12, IL-18, GMCSF, IFNγ, MCP-1 and CXCL9, also known as Monokine induced by gamma interferon (MIG), to CHIKV clearance and disease resolution in humans, monkeys, and mice (see, Chaaitanya, L K., et al., 2011 Viral immunology 24:265-271; Chow, A., et al., 2011 The Journal of infectious diseases 203:149-157; Couderc, T., et al., 2008 PLoS pathogens 4:e29; Kelvin, A. A., et al., 2011 PLoS neglected tropical diseases 5:e1279; Messaoudi, I., et al., 2013 PLoS neglected tropical diseases 7:e2343; Ng, L. F., et al., 2009 PloS one 4:e4261). Type I IFN (a/(3) was specifically identified as a key mediator regulating clearance in both mouse and macaque models (see, Gardner, C. L., et al., Virology 425:103-112; Messaoudi, I., et al., PLoS neglected tropical diseases 7:e2343). However, a robust local pro-inflammatory response early after infection also contributes to the arthritic manifestation of the disease through the synergistic action of IL-1β and IL-6 (see, Ng, L. F., et al., 2009 PloS one 4:e4261); the extent of pathogenesis vs. clearance mediated by individual cytokines and chemokines is still unknown. Immune cell subset contributions have also been evaluated. Synovial macrophages are required for both dissemination of virus and mediation of local inflammation, and their depletion resulted in disease amelioration (see, Hoarau, J. J., et al., 2010 Journal of immunology (Baltimore, Md.: 1950) 184: 5914-5927; Kumar, S., et al., 2012 Virology journal 9:313). T cells are required for the characteristic swelling of the joints measured in mouse models as well as for full clearance of virus (see, Hawman, D. W., et al., 2013 Journal of virology 87:13878-13888; Teo, T. H., et al., 2013 Journal of immunology (Baltimore, Md.: 1950) 190:259-269). B cell populations increase in numbers in the footpads of infected mice and passive transfer of antibodies can clear infection, supporting the importance of humoral CHIKV immunity (see, Gardner, J., et al., 2010 Journal of virology 84:8021-8032; Pal, P., et al., 2013 PLoS pathogens 9:e1003312). Despite all of these studies it is still unclear how the innate response coordinates the adaptive response during CHIKV infection; what the impact of that response may be on disease severity, and how that may be altered in the context of specific risk-factors such as age.

Despite the above advances, it remains unknown why certain individuals and populations experience more severe and/or persistent disease and what specific immune defects may contribute to increased susceptibility. It has been shown that older adults are at greater risk of persistent and severe CHIKV disease, likely due to one or more defects affecting the innate and adaptive immune response in aging. Understanding such defects would be the first key step towards potential immune modulation to improve CHIKV disease outcomes. A mouse model was developed which recapitulates age-related clinical outcomes observed in CHIKV-infected elderly humans, and used it to elucidate mechanisms underlying the age-related dysfunction of the immune response to CHIKV infection. Such experiments demonstrated increased local production of TGF at the innate level ultimately leads to both a qualitative and quantitative impairment of B and T cell responses which fail to clear the virus and exacerbate disease pathology. It was further shown that anti-TGFβ antibody blockade can successfully prevent age-related increased CHIKV disease severity, suggesting one possible avenue in treating CHIKV infection in older adults.

Accordingly, the present invention provides methods and pharmaceutical compositions for preventing, treating or suppressing symptoms of a disorder associated with an alphavirus infection. In particular, the present invention relates to preventing, treating or suppressing symptoms of a disorder associated with an alphavirus infection through inhibiting the activity and/or expression of TGF-β in a subject suffering from or at risk for suffering from an alphavirus infection.

The present invention provides monotherapy and combination therapy methods of treating an alphavirus infection. In some embodiments, the present invention provides methods of reducing the incidence of complications associated with alphaviral infection in subjects suffering from alphaviral infection. In some embodiments, such methods are amenable to treatment in a subject (e.g., a human patient). In other embodiments, such methods are applicable to alphaviruses present in a medium. The methods generally involve administering to a culture containing an alphavirus or a subject an effective amount of an agent that inhibits one or more functional activities of TGF-β via a monotherapy or a combination therapy. Effective amounts of an agent that inhibits TGF-β activity, as well as dosing regimens, are discussed below. In general, an effective amount of an agent that inhibits one or more functional activities of TGF-β is an amount that is effective to reduce symptoms related to alphavirus infection.

In one embodiment, the method involves administering an effective amount of an agent that inhibits one or more functions of TGF-β. Whether a subject monotherapy method is effective in treating an alphaviral infection can be determined by measuring a parameter associated with alphaviral infection, including, but not limited to, encephalitis, arthritis, rashes, fevers, headache, nausea, myalgia, arthralgia (joint pain), arthropathy (diseases of the joint), chills, diarrhea, vomiting, lymphadenitis, malaise, and muscle soreness, according to well known methods in the art.

Generally, the methods described herein are suitable for treating subjects having, or susceptible to having an alphavirus infection. The subject methods are also suitable for treating subjects who have been previously treated for an alphavirus infection with an agent other than a TGF-β inhibitor and are refractory to treatment with the agent, and who have either failed the previous treatment; or who cannot tolerate treatment with the non-TGF-β inhibitor; or who responded to the previous treatment and relapsed. In many embodiments, the individual is a human.

Subjects who have been clinically diagnosed as infected with an alphavirus are suitable for treatment with a method of the instant invention. Of particular interest in some embodiments are subjects who have been clinically diagnosed as infected with an alphavirus (e.g., clinically diagnosed as having CHIKV).

Subjects who are clinically diagnosed as infected with an alphavirus infection include naïve subjects (e.g., subjects who have not previously treated for alphaviral infection) and subjects who have failed prior treatment for alphaviral ("treatment failure" subjects) can be treated using the methods described herein. Treatment failure subjects include non-responders (i.e., subjects in whom the alphaviral titer was not significantly or sufficiently reduced by a previous treatment for alphaviral infection and relapsers). Also of interest are alphaviral-positive subjects who exhibit symptoms consistent with alphaviral infection but who have not yet been clinically diagnosed or who are viremic despite prior antiviral treatments or who have a contraindication to standard antiviral treatments.

Agents that are suitable for use in a subject treatment method are agents that inhibits the activity of one or more functions of TGF-β. An agent that is suitable for use in a subject monotherapy is an agent the can inhibit the one or more functions of TGF-β by at least about 10%, at least about 15%, at least about 20%, at least about 25%, at least about 30%, at least about 35%, at least about 40%, at least about 50%, at least about 60%, at least about 70%, at least about 80%, or at least about 90%, or more, compared to the activity of TGF-β in the absence of the agent.

A variety of TGF-β inhibitors and methods for their production are well known in the art and many more are currently under development. The specific TGF-β antagonist employed is not a limiting feature; any effective TGF-β antagonist as defined herein may be useful in the methods and compositions of this invention. Preferably, the TGF-β antagonist is a TGF-β1, TGF-132, or TGF-β3 antagonist.

Examples of TGF-β antagonists include, but are not limited to: monoclonal and polyclonal antibodies directed against one or more isoforms of TGF-β (see, e.g., U.S. Pat. No. 5,571,714; Thompson et al., 1997 WO/97/13844 and & 2000, WO00/66631); TGF-β receptors or antibodies directed against TGF-β receptors (see, e.g., U.S. Pat. Nos. 5,693,607; 6,001,969; 6,008,011; 6,010,872; WO 92/00330; WO 93/09228; WO 95/10610; and WO 98/48024); TGF-β antibody clone 1D11.16.8; latency associated peptide (see, e.g., WO 91/08291); large latent TGF-β (see, e.g., WO 94/09812); decorin and other proteoglycans such as biglycan, fibromodulin, lumican and endoglin (see, e.g., U.S. Pat. Nos. 5,583,103; 5,654,270; 5,705,609; 5,726,149; 5,824,655; 5,830,847; 6,015,693; US WO 91/04748; U.S. Pat. No. 5,583,103; WO 93/09800; and WO 94/10187); somatostatin (see, e.g., WO 98/08529); mannose-6-phosphate or mannose-1-phosphate (see, e.g., U.S. Pat. No. 5,520,926); prolactin (see, e.g., WO 97/40848); insulin-like growth factor II (see, e.g., WO 98/17304); IP-10 (see, e.g., WO 97/00691); arg-gly-asp containing peptides (see, e.g., U.S. Pat. No. 5,958,411; WO 93/10808); extracts of plants, fungi and bacteria (see, e.g., EU 813875; JP 8119984; and U.S. Pat. No. 5,693,610); antisense oligonucleotides (see, e.g., U.S. Pat. Nos. 5,683,988; 5,772,995; 5,821,234; 5,869,462; and WO 94/25588); proteins involved in TGF-β signaling, including Smads and MADs (see, e.g., EP 874046; WO 97/31020; WO 97/38729; WO 98/03663; WO 98/07735; WO 98/07849; WO 98/45467; WO 98/53068; WO 98/55512; WO 98/56913; WO 98/53830; WO 99/50296; U.S. Pat. Nos. 5,834,248; 5,807,708; and 5,948,639), Ski and Sno (see, e.g., Vogel, 1999, Science 286:665; and Stroschein et al., 1999, Science 286:771-774); and any mutants, fragments or derivatives of the above-identified molecules that retain the ability to inhibit the activity of TGF-β.

The TGF-β antagonist may be a human or humanized monoclonal antibody that blocks TGF-β binding to its receptor, or fragments thereof such as F(ab), fragments, Fv fragments, single chain antibodies and other forms of "antibodies" that retain the ability to bind to TGF-β. In one embodiment, the TGF-β antagonist is a human antibody produced by phage display (see, e.g., WO 00/66631).

Mutants, variants, derivatives, and analogues of the aforementioned TGF-β antagonist may also be useful in the methods of this invention. As used herein, "mutants, variants, derivatives and analogues" refer to molecules with similar shape or structure to the parent compound and that retain the ability to act as TGF-β antagonists. For example, any of the TGF-β antagonists disclosed herein may be crystallized, and useful analogues may be rationally designed based on the coordinates responsible for the shape of the active site(s). Alternatively, the ordinarily skilled artisan may, without undue experimentation, modify the functional groups of a known antagonist and screen such modified molecules for increased activity, half-life, bioavailability, or other desirable characteristics. Where the TGF-β antagonist is a polypeptide, fragments and modifications of the polypeptide may be produced to increase the ease of delivery, activity, half-life, etc (for example, humanized antibodies or functional antibody fragments, as discussed above). Given the level of skill in the art of synthetic and recombinant polypeptide production, such modifications may be achieved without undue experimentation.

The present invention may also employ a vector suitable for expression of a TGF-β receptor or binding partner, preferably a soluble receptor or binding partner. More preferably, administration of a soluble TGF-β antagonist is effected by gene transfer using a vector comprising cDNA encoding the soluble antagonist, most preferably cDNA encoding the extracellular domain of TGF-β type II (rsTGFBIIR) or type III receptor (rsTGFBIIIR), which vector is administered, preferably topically, to a donor organ to cause in situ expression of the soluble TGF-β antagonist in cells of the organ transfected with the vector. Such in situ expression inhibits the activity of TGF-β and curbs TGF-β-mediated fibrogenesis. Any suitable vector may be used. Preferred vectors include adenovirus, lentivirus, Epstein Barr virus (EBV), adeno associated virus (AAV), and retroviral vectors that have been developed for the purpose of gene transfer (see, e.g., Souza and Armentano, 1999, Biotechniques, 26:502-508). Other, non-vector methods of gene transfer may also be used, for example, lipid/DNA complexes, protein/DNA conjugates, naked DNA transfer methods, and the like. Antisense to a TGF-β receptor may also be administered (see, e.g., Lenferink A E, et al., Int J. Cancer. 2003 Dec. 20; 107(6):919-28).

Additional suitable TGF-β antagonists developed for delivery via adenoviral gene transfer include, but are not limited to: a chimeric cDNA encoding an extracellular domain of the TGF-β type II Receptor fused to the Ig Fc domain (see, e.g., Isaka et al., 1999, Kidney Int., 55:465-475), adenovirus gene transfer vector of a dominant-negative mutant of TGF-β type H Receptor (see, e.g., Zhao et al, 1998, Mech. Dev., 72:89-100.), and an adenovirus gene transfer vector for decorin, a TGF-β binding proteoglycan (see, e.g., Zhao et al., 1999, Am. J. Physiol., 277:L412-L422). Adenoviral-mediated gene transfer is very high efficiency compared to other gene delivering modalities. However, in vivo gene transfer using adenoviral vectors as a therapeutic modality has been limited by the host immune response that induces inflammation, limits the amount and duration of transgene expression, and prevents effective re-transfection.

Of particular interest in some embodiments of a subject monotherapy is use of an agent that inhibits one or more functions of TGF-β with an $IC_{50}$ of less than about 50 µM, e.g., a suitable agent inhibits TGF-β activity with an $IC_{50}$ of less than about 40 µM, less than about 25 µM, less than about 10 µM, less than about 1 µM, less than about 100 nM, less than about 80 nM, less than about 60 nM, less than about 50 nM, less than about 25 nM, less than about 10 nM, or less than about 1 nM, or less.

In many embodiments, an agent that inhibits one or more TGF-β functions also inhibits alphaviral replication. For example, an agent that inhibits TGF-β inhibits viral replication by at least about 10%, at least about 15%, at least about 20%, at least about 25%, at least about 30%, at least about 40%, at least about 50%, at least about 60%, at least about 70%, at least about 80%, or at least about 90%, or more, compared to alphaviral replication in the absence of the TGF-β inhibitor. Whether a TGF-β inhibitor inhibits viral replication can be determined using methods known in the art, including an in vitro viral replication assay.

Whether treatment with an agent that inhibits one or more TGF-β functions is effective in treating symptoms of alphaviral infection (e.g., encephalitis, arthritis, rashes, fevers, headache, nausea, myalgia, arthralgia (joint pain), arthropathy (diseases of the joint), chills, diarrhea, vomiting, lymphadenitis, malaise, and muscle soreness) can be determined by any of a number of techniques well known in the art. In some embodiments, an effective amount of an agent that inhibits TGF-β activity is an amount that is effective to reduce a symptom of alphaviral infection (e.g., encephalitis, arthritis, rashes, fevers, headache, nausea, myalgia, arthralgia (joint pain), arthropathy (diseases of the joint), chills, diarrhea, vomiting, lymphadenitis, malaise, and muscle soreness) by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, or more, compared to that in an untreated subject, or to a placebo-treated subject. Those skilled in the art can readily measure such indices of alphaviral symptoms, using standard assay methods, many of which are commercially available, and are used routinely in clinical settings.

Indirect markers of alphaviral infection symptoms can also be measured as an indication of the efficacy of a subject treatment method. For example, markers of inflammation, such as TNF-alpha, IL-1 beta, and IL-20, can be analyzed as an indirect marker of arthritis. Those skilled in the art can readily measure such markers using standard assay methods, many of which are commercially available, and are used routinely in clinical settings. Methods of measuring such markers include nucleic acid-based detection methods and immunological-based methods, e.g., enzyme-linked immunosorbent assays (ELISA), radioimmunoassays, and the like, using an antibody specific for a given serum marker.

The effectiveness of any particular TGF-β inhibitor or second therapeutic agent to treat alphaviral infection can be monitored by comparing two or more samples obtained from a subject undergoing treatment. In general, it is preferable to obtain a first sample from the subject prior to beginning therapy and one or more samples during treatment. In such a use, a baseline of antiviral effects of cells from subjects infected with an alphavirus prior to therapy is determined and then changes in the baseline state of expression of cells from subjects infected with the alphavirus is monitored during the course of therapy. Alternatively, two or more successive samples obtained during treatment can be used without the need of a pre-treatment baseline sample.

The present invention further provides combination therapies. Although no FDA-approved therapeutics or vaccines have been approved specifically to target alphaviral infection, the present invention provides methods for combining TGF-β inhibitors with at least a second therapeutic agent. In some embodiments, the at least a second therapeutic agent is a therapeutic that inhibits viral replication.

In other embodiments, the at least a second therapeutic is a therapeutic that ameliorates one or more symptoms of alphaviral infection. As with monotherapy methods described above, combination therapies generally involve administering to a subject in need thereof an effective amount of an agent that inhibits one or more functions of TGF-β activity, in combination with at least a second therapeutic agent. In some embodiments, the second therapeutic agent is effective to reduce viral replication, or reduce the time to viral clearance, or an amount that is effective to reduce morbidity or mortality in the clinical course of the disease, or an amount that is effective to improve some other indicator of disease response (e.g., an amount that is effective to reduce viral load; achieve a sustained viral response; etc.).

Suitable second therapeutic agents for treating an alphavirus infection include, but are not limited to, a nucleoside analog (e.g., ribavirin, levovirin, viramidine), mycophenolic acid, inhibitors of inosine monophosphate dehydrogenase (IMPDH); anti-alphaviral, neutralizing monoclonal antibodies (see, for example, U.S. Pat. No. 6,812,329); interferon alpha (see, for example, US Pat. Publ. 2006/0024270); poly ICLC (i.e., a synthetic complex of carboxymethylcellulose, polyinosinic-polycytidylic acid, and poly-L-lysine double-stranded RNA; Wong et al. (2005) Vaccine 23:2266-2268); triaryl pyrazolin (see, for example, Puig-Basagoiti et al. (2006) Antimicrob. Agents Chemother. 50:1320-1329); ribozymes that are complementary to viral nucleotide sequences (see, for example, Seyhan et al. (2002) J. Biol.

Chem. 277:25957-25962); zinc-finger antiviral protein (see, for example, Bick et al. (2003) J. Virol. 77:11555-11562); human lactoferrin (Waarts et al. (2005) Virol. 333:284-292); antisense RNA inhibitors; and the like.

For example, nucleoside analogs for use as antiviral agents are well known in the art. Nucleoside analogs that are suitable for use in a subject combination therapy include, but are not limited to, ribavirin, levovirin, viramidine, isatoribine, an L-ribofuranosyl nucleoside as disclosed in U.S. Pat. No. 5,559,101 and encompassed by Formula I of U.S. Pat. No. 5,559,101 (e.g., 1-β-L-ribofuranosyluracil, 1-β-L-ribofuranosyl-5-fluorouracil, 1-β-L-ribofuranosylcytosine, 9β-L-ribofuranosyladenine, 9β-L-ribofuranosylhypoxanthine, 9β-L-ribofuraosylguanine, 9β-L-ribofuranosyl-6-thioguanine, 2-amino-α-L-ribofuran[1',2':4,5]oxazoline, $O^2,O^2$-anhydro-1-α-L-ribofuranosyluracil, 1-α-L-ribofuranosyluracil, 1-(2,3,5-tri-O-benzoyl-α-ribofuranosyl)-4-thiouracil, 1-α-L-ribofuranosylcytosine, 1-α-L-ribofuranosyl-4-thiouracil, 1-α-L-ribofuranosyl-5-fluorouracil, 2-amino-β-L-arabinofurano[1',2':4,5]oxazoline, $O^2,O^2$-anhydro-β-L-arabinofuranosyluracil, 2'-deoxy-β-L-uridine, 3'5'-Di-O-benzoyl-2' deoxy-4-thio 2'-deoxy-β-L-cytidine, 2'-deoxy-β-L-4-thiouridine, 2'-deoxy-β-L-thymidine, 2'-deoxy-β-L-5-fluorouridine, 2'-deoxy-β-L-5-fluorouridine, and 2'-deoxy-β-L-inosine); a compound as disclosed in U.S. Pat. No. 6,423,695 and encompassed by Formula I of U.S. Pat. No. 6,423,695; a compound as disclosed in U.S. Patent Publication No. 2002/0058635, and encompassed by Formula I of U.S. Patent Publication No. 2002/0058635; a nucleoside analog as disclosed in WO 01/90121 A2 (Idenix); a nucleoside analog as disclosed in WO 02/069903 A2 (Biocryst Pharmaceuticals Inc.); a nucleoside analog as disclosed in WO 02/057287 A2 or WO 02/057425 A2 (both Merck/Isis); and the like. The nucleoside analogs may be administered orally in capsule or tablet form, or in the same or different administration form and in the same or different route as the cyclophilin inhibitor. Of course, other types of administration of both medicaments, as they become available are contemplated, such as by nasal spray, transdermally, by suppository, by sustained release dosage form, etc. Any form of administration will work so long as the proper dosages are delivered without destroying the active ingredient.

In some embodiments, mycophenolic acid (Malinoski et al. (1981) Virol. 110:281-289), carbodine, triaryl pyrazoline (Puig-Basagoiti et al. (2006) Antimicrob. Agents Chemother 50:1320-1329) or seco-pregnane steroids from the Chinese herbs *Strobilanthes cusia* and *Cynanchum paniculatum* (Li et al., (2007) Proc. Natl. Acad. Sci. USA 104:8083-8038) can be used to inhibit alphavirus replication.

IMPDH inhibitors that are suitable for use in a subject combination therapy include, but are not limited to, VX-497 ((S)—N-3-[3-(3-methoxy-4-oxazol-5-yl-phenyl)-ureido]-benzyl-carbamic acid tetrahydrofuran-3-yl-ester); Vertex Pharmaceuticals; see, e.g., Markland et al. (2000) Antimicrob. Agents Chemother. 44:859-866); and the like.

Ribozyme and antisense antiviral agents that are suitable for use in a subject combination therapy include, but are not limited to, ISIS 14803 (ISIS Pharmaceuticals/Elan Corporation; see, e.g., Witherell (2001) Curr Opin Investig Drugs. 2(11):1523-9); Heptazyme™; and the like.

Any means for the introduction of such polynucleotides into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat. Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject.

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxvirus, an arena virus, a vaccinia virus, a polio virus, and the like. They offer several attractive features for various mammalian cells (Friedmann (1989) Science, 244:1275-1281; Coupar et al., 1988; Horwich et al. (1990) J. Virol., 64:642-650).

In other embodiments, a subject therapy further comprises administering a palliative agent (e.g., an agent that reduces patient symptoms caused by the alphaviral infection), or other agent for the avoidance, treatment, or reduction of a side effect of a therapeutic agent. Such agents are also referred to as "symptom management agents" or "side effect management agents." Suitable symptom management agents include agents that reduce one or more patient symptoms caused by the alphaviral infection. Suitable side effect management agents include agents for the avoidance, treatment, or reduction of a side effect of an agent that inhibits TGF-β activity; agents for the avoidance, treatment, or reduction of a side effect of a therapeutic agent.

Suitable symptom and/or side effect management agents include agents that are effective in pain management; agents that ameliorate gastrointestinal discomfort; analgesics, anti-inflammatories, antipsychotics, antineurotics, anxiolytics, and hematopoietic agents. In addition, the invention contemplates the use of any compound for palliative care of subjects suffering from pain or any other side effect in the course of treatment with a subject therapy. Exemplary palliative agents include acetaminophen, ibuprofen, and other NSAIDs, H2 blockers, and antacids.

Analgesics that can be used to alleviate pain in the methods of the invention include non-narcotic analgesics such as non-steroidal anti-inflammatory drugs (NSAIDs) acetaminophen, salicylate, acetyl-salicylic acid (aspirin, diflunisal), ibuprofen, Motrin, Naprosyn, Nalfon, and Trilisate, indomethacin, glucametacine, acemetacin, sulindac, naproxen, piroxicam, diclofenac, benoxaprofen, ketoprofen, oxaprozin, etodolac, ketorolac tromethamine, ketorolac, nabumetone, and the like, and mixtures of two or more of the foregoing.

Other suitable analgesics include fentanyl, buprenorphine, codeine sulfate, morphine hydrochloride, codeine, hydromorphone (Dilaudid), levorphanol (Levo-Dromoran), methadone (Dolophine), morphine, oxycodone (in Percodan), and oxymorphone (Numorphan). Also suitable for use are benzodiazepines including, but not limited to, flurazepam (Dalmane), diazepam (Valium), and Versed, and the like.

Suitable anti-inflammatory agents include, but are not limited to, steroidal anti-inflammatory agents, and non-steroidal anti-inflammatory agents. For example, suitable steroidal anti-inflammatory agents include, but are not limited to, hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, conisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures of two or more of the foregoing. In other embodiments, suitable non-steroidal anti-inflammatory agents, include, but are not limited to, 1) the oxicams, such as piroxicam, isoxicam, tenoxicam, and sudoxicam; 2) the salicylates, such as aspirin, disalcid, benorylate, trilisate, safapryn, solprin, and fendosal; 3) the acetic acid derivatives, such as diclofenac, fenclofenac, indomethacin, sulindac, tolmetin, isoxepac, furofenac, tiopinac, zidometacin, acematacin, fentiazac, zomepiract, clidanac, oxepinac, and felbinac; 4) the fenamates, such as mefenamic, meclofenamic, flufenamic, niflumic, and tolfenamic acids; 5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, al:minoprofen, and tiaprofenic; and 6) the pyrazoles, such as phenylbutazone, oxyphenbutazone, feprazone, azapropazone, and trimethazone, mixtures of these non-steroidal anti-inflammatory agents may also be employed, as well as the pharmaceutically-acceptable salts and esters of these agents.

Other suitable anti-inflammatory agents include, but are not limited to, Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin. Sodium; Triclonide; Triflumidate; Zidometacin; and Zomepirac Sodium.

Antipsychotic and antineurotic drugs that can be used to alleviate psychiatric side effects in the methods of the invention include any and all selective serotonin receptor inhibitors (SSRIs) and other anti-depressants, anxiolytics (e.g. alprazolam), etc. Anti-depressants include, but are not limited to, serotonin reuptake inhibitors such as Celexa®, Desyrel®, Effexor®, Luvox®, Prozac®, Zoloft®, and Serzone®; tricyclics such as Adapin®, Anafrinil®, Janimmine®, Ludiomil®, Pamelor®, Tofranil®, Vivactil®, Sinequan®, and Surmontil®; monoamine oxidase inhibitors such as Eldepryl®, Marplan®, Nardil®, and Parnate®. Anti-anxiety agents include, but are not limited to, azaspirones such as BuSpar®, benzodiazepines such as Ativan®, Librium®, Tranxene®, Centrax®, Klonopin®, Paxipam®, Serax®, Valium®, and Xanax®; and beta-blockers such as Inderal® and Tenormin®.

Agents that reduce gastrointestinal discomfort such as nausea, diarrhea, gastrointestinal cramping, and the like are suitable palliative agents for use in a subject combination therapy. Suitable agents include, but are not limited to, antiemetics, anti-diarrheal agents, H2 blockers, antacids, and the like.

Suitable H2 blockers (histamine type 2 receptor antagonists) that are suitable for use as a palliative agent in a subject therapy include, but are not limited to, Cimetidine (e.g., Tagamet, Peptol, Nu-cimet, apo-cimetidine, non-cimetidine); Ranitidine (e.g., Zantac, Nu-ranit, Novo-randine, and apo-ranitidine); and Famotidine (Pepcid, Apo-Famotidine, and Novo-Famotidine).

Suitable antacids include, but are not limited to, aluminum and magnesium hydroxide (Maalox®, Mylanta®); aluminum carbonate gel (Basajel®); aluminum hydroxide (Amphojel®, AlternaGEL®); calcium carbonate (Tums®, Titralac®); magnesium hydroxide; and sodium bicarbonate.

Antiemetics include, but are not limited to, 5-hydroxytryptophan-3 (5HT3) inhibitors; corticosteroids such as dexamethasone and methylprednisolone; Marinol® (dronabinol); prochlorperazine; benzodiazepines; promethazine; and metoclopramide cisapride; Alosetron Hydrochloride; Batanopride Hydrochloride; Bemesetron; Benzquinamide; Chlorpromazine; Chlorpromazine Hydrochloride; Clebopride; Cyclizine Hydrochloride; Dimenhydrinate; Diphenidol; Diphenidol Hydrochloride; Diphenidol Pamoate; Dolasetron Mesylate; Domperidone; Dronabinol; Fludorex; Flumeridone; Galdansetron Hydrochloride; Granisetron; Granisetron Hydrochloride; Lurosetron Mesylate; Meclizine Hydrochloride; Metoclopramide Hydrochloride; Metopimazine; Ondansetron Hydrochloride; Pancopride; Prochlorperazine; Prochlorperazine Edisylate; Prochlorperazine Maleate; Promethazine Hydrochloride; Thiethylperazine; Thiethylperazine Malate; Thiethylperazine Maleate; Trimethobenzamide Hydrochloride; Zacopride Hydrochloride.

Anti-diarrheal agents include, but are not limited to, Rolgamidine, Diphenoxylate hydrochloride (Lomotil), Metronidazole (Flagyl), Methylprednisolone (Medrol), Sulfasalazine (Azulfidine), and the like.

Suitable hematopoietic agents that can be used to prevent or restore depressed blood cell populations in the methods of the invention include erythropoietins, such as EPOGEN™ epoetin-alfa, granulocyte colony stimulating factors (G-CSFs), such as NEUPOGEN™ filgrastim, granulocyte-macrophage colony stimulating factors (GM-CSFs), thrombopoietins, etc.

An active agent (e.g., a TGF-β inhibitor, at least one additional therapeutic agent, etc.) can be administered to subjects in a formulation with a pharmaceutically acceptable excipient(s). The terms "active agent" and "therapeutic agent" are used interchangeably herein. A wide variety of pharmaceutically acceptable excipients are known in the art and have been. well described in a variety of publications, including, for example, A. Gennaro (2000) "Remington: The Science and Practice of Pharmacy," 20th edition, Lippincott, Williams, & Wilkins Pharmaceutical Dosage Forms and Drug Delivery Systems (1999) H. C. Ansel et al., eds., 7th ed., Lippincott, Williams, & Wilkins and Handbook of Pharmaceutical Excipients (2000) A. H. Kibbe et al., eds., 3rd ed. Amer. Pharmaceutical Assoc. Pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In the subject methods, an active agent (e.g., a TGF-β inhibitor, at least one additional therapeutic agent, etc.) may be administered to the host using any convenient means capable of resulting in the desired therapeutic effect. Thus, an active agent can be incorporated into a variety of formulations for therapeutic administration. More particularly, an active agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of an active agent can be achieved in various ways, including oral, buccal, rectal, parenteral, intraperitoneal, intradermal, subcutaneous, intramuscular, transdermal, intratracheal, etc., administration. In some embodiments, two different routes of administration can be used.

Subcutaneous administration of an active agent (e.g., a TGF-β inhibitor, at least one additional therapeutic agent, etc.) can be accomplished using standard methods and devices, e.g., needle and syringe, a subcutaneous injection port delivery system, and the like. See, e.g., U.S. Pat. Nos. 3,547,119; 4,755,173; 4,531,937; 4,311,137; and 6,017,328. A combination of a subcutaneous injection port and a device for administration of a therapeutic agent to a patient through the port is referred to herein as "a subcutaneous injection port delivery system." In some embodiments, subcutaneous administration is achieved by a combination of devices, e.g., bolus delivery by needle and syringe, followed by delivery using a continuous delivery system. Such delivery methods may be especially useful for administration to cell types in the CNS.

In some embodiments, an active agent (e.g., a TGF-β inhibitor, at least one additional therapeutic agent, etc.) is delivered by a continuous delivery system. The terms "continuous delivery system," "controlled delivery system," and "controlled drug delivery device," are used interchangeably to refer to controlled drug delivery devices, and encompass pumps in combination with catheters, injection devices, and the like, a wide variety of which are known in the art. Such delivery methods may be especially useful for administration to cell types in the CNS.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

For oral preparations, an active agent (e.g., a TGF-β inhibitor, at least one additional therapeutic agent, etc.) is formulated alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives, and flavoring agents. Furthermore, an active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the agent(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an active agent (e.g., a TGF-β inhibitor, at least one additional therapeutic agent, etc.) calculated in an amount sufficient to produce the desired effect in association with a pharmaceutically acceptable diluent, carrier or vehicle. The specifications for the unit dosage forms depend on the particular agent employed and the effect to be achieved, and the pharmacodynamics associated with each agent in the host.

In some embodiments, an active agent (e.g., a TGF-β inhibitor, at least one additional therapeutic agent, etc.) is administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time.

The amount of active ingredient (e.g., an agent that inhibits one or more TGF-β functions) that may be combined with carrier materials to produce a dosage form can vary depending on the host to be treated and the particular mode of administration. A typical pharmaceutical preparation can contain from about 5% to about 95% active ingredient (w/w), and in some cases from about 95% to about 98%, or from about 98% to about 99% (w/w) active ingredient). In other embodiments, the pharmaceutical preparation can contain from about 20% to about 80% active ingredient.

Those of skill will readily appreciate that dose levels can vary as a function of the specific agent that inhibits one or more TGF-β functions, the severity of the symptoms and the susceptibility of the subject to side effects. Preferred dosages for a given agent that inhibits TGF-13 activity are readily determinable by those of skill in the art by a variety of means. A typical means is to measure the physiological potency of a given active agent.

In some embodiments, multiple doses of an agent that inhibits TGF-β activity are administered. For example, an agent that inhibits TGF-β activity is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

In some embodiments of combination therapies, the additional antiviral agent(s) can be administered during the entire course of treatment with a TGF-β inhibitor, and the beginning and end of the treatment periods coincide. In other embodiments, the additional antiviral agent(s) is administered for a period of time that is overlapping with that of the TGF-β inhibitor treatment, e.g., treatment with the additional antiviral agent(s) begins before the TGF-β inhibitor treatment begins and ends before the TGF-β inhibitor treatment ends; treatment with the additional antiviral agent(s) begins after the TGF-β inhibitor treatment begins and ends after the TGF-β inhibitor treatment ends; treatment with the additional antiviral agent(s) begins after the TGF-β inhibitor treatment begins and ends before the TGF-β inhibitor treatment ends; or treatment with the additional antiviral agent(s) begins before the TGF-β inhibitor treatment begins and ends after the TGF-β inhibitor treatment ends.

The TGF-β inhibitor can be administered together with (i.e., simultaneously in separate formulations; simultaneously in the same formulation; administered in separate formulations and within about 48 hours, within about 36 hours, within about 24 hours, within about 16 hours, within about 12 hours, within about 8 hours, within about 4 hours, within about 2 hours, within about 1 hour, within about 30 minutes, or within about 15 minutes or less) one or more additional antiviral agents.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

Age Increases Acute CHIKV-Induced Joint Swelling

Experimental footpad (f.p.) CHIKV infection results in biphasic swelling of the foot and ankle joint over the acute period of infection from day 2 to 16, when measurable swelling is resolved (see, Pal, P., et al., 2013 PLoS pathogens 9:e1003312; Teo, T. H., et al., 2013 Journal of immunology (Baltimore, Md.: 1950) 190:259-269). In such studies, no swelling was observed in the contralateral non-inoculated or saline-injected foot, and because there were no differences between these two controls, non-inoculated control (CTRL) was used throughout the study. Importantly, old (O) mice exhibit significantly increased swelling as compared to adult (A) during both the innate and adaptive phases of the immune response (FIG. 1). In addition, in 0 mice peak swelling in both phases was sustained longer and at higher levels than in A animals (FIG. 1). Overall, there were no kinetic difference in the timing of disease onset or resolution of swelling between A and O mice, which occurred in both groups by day 16 post-infection (FIG. 1). There was no CHIKV-specific mortality in either age group.

Example II

Old Mice Exhibit Delayed and Incomplete CHIKV Clearance

Figure 2:
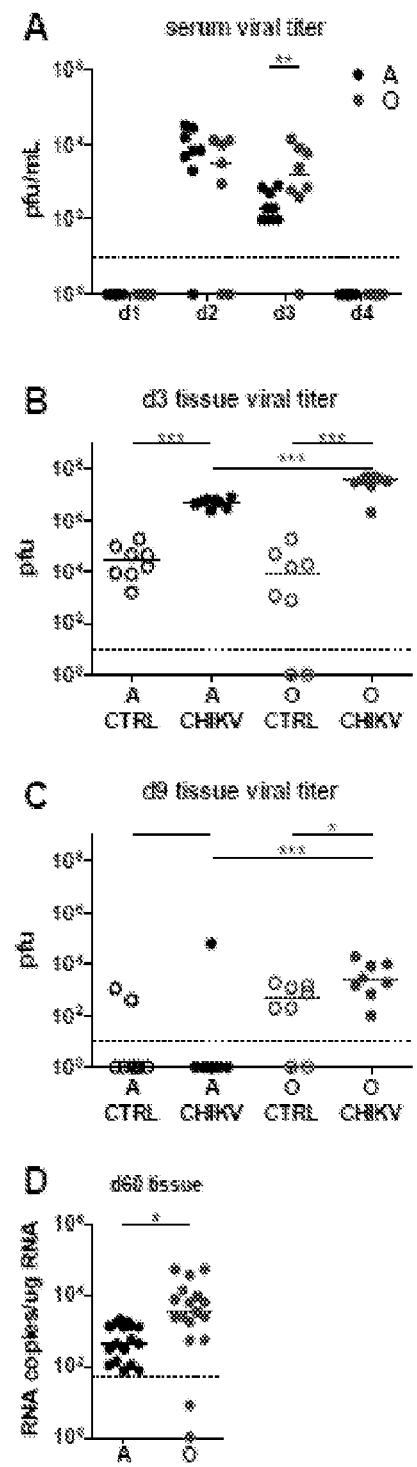

To determine whether increased foot swelling in 0 CHIKV infected mice could be attributed to increased viremia experiments were conducted which measured viral titers in the serum, inoculated foot, and non-inoculated foot by plaque assay. Differences in serum viral titers were not detected between O and A mice on day's 1-2 post infection (FIG. 2A). There were higher viral loads in the serum of O mice on day 3 but full resolution in both O and A mice by day 4, suggesting delayed viral clearance in O mice (FIG. 2A). Delayed clearance is supported by a measured 10 fold higher viral load in the inoculated feet of O mice as compared to A on day 3 post-infection (FIG. 2B). Despite the absence of joint swelling, CHIKV was also detectable at this time point in the control, non-inoculated, foot at approximately 1000 fold lower levels as compared to the inoculated foot. By day 9 post infection, the virus was generally cleared from the feet of A mice but remained detectable in the feet of the O animals (FIG. 2C). Finally, viral genomes could be detected in the tissues of both A and O mice on day 60 post-infection with significantly higher viral genome copies in the O mice (FIG. 2D). Taken together these results demonstrate impaired virus control with aging. While delayed viral clearance in O mice may contribute to increased swelling and other virus induced joint pathologies, viral load cannot be the sole determining factor for swelling because viral titers on day 9, when there is quite a lot of swelling, were markedly lower than on day 3.

Example III

Age-Related Impairment of Cellular Recruitment to Draining Lymph Node

Figure 3A:
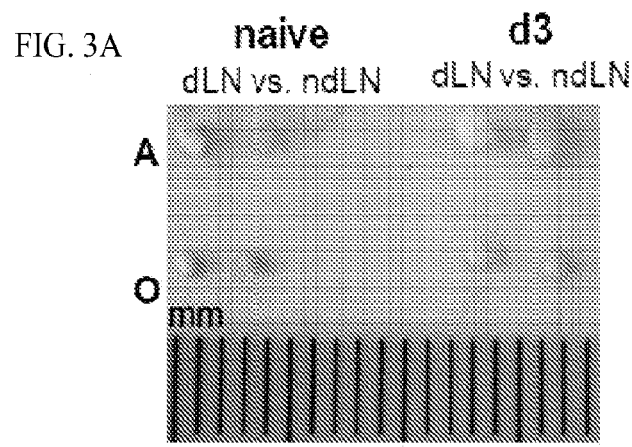

The above findings prompted us to ask whether there is a defect in the recruitment of a sufficient quantity and/or quality of lymphocytes in O mice to contribute to viral clearance and potentiate an effective immune response. To begin, experiments simply evaluated the gross size of naïve popliteal LNs from A and O mice. Naïve LNs from old mice are visibly smaller than those in A mice (FIG. 3A). Further, despite a marked increase in the size of both the draining and non-draining O LN on day 3 of CHIKV infection there is a failure to recover fully the size discrepancy with age (FIG. 3A). This suggests an inability of the O LN to expand, recruit, or maintain a sufficient number of cells to make up the naïve deficit. Using FCM analysis such experiments next identified the specific immune cell subsets responding to CHIKV-infection and determined the extent of the age-related quantitative and qualitative defects. The strategy used to understand the FCM data first involved measuring and comparing the total number of each cell type in the draining and non-draining LNs of naïve and CHIKV-infected A and O mice. At each time-point post-infection the relative fold-increase over the average for naïve mice of the same age was determined. This allowed an answering of three critical questions: First, which cell types are lost with age? Second, which (if any) cell types can be recruited or expanded in 0 mice during CHIKV-infection to equal the numbers and/or quality measured in adult? Third, do O mice increase cellular numbers to the same relative extent of A mice (as demonstrated by fold-change) but simply cannot overcome the deficiency of fewer numbers to start with?

Figure 3B:
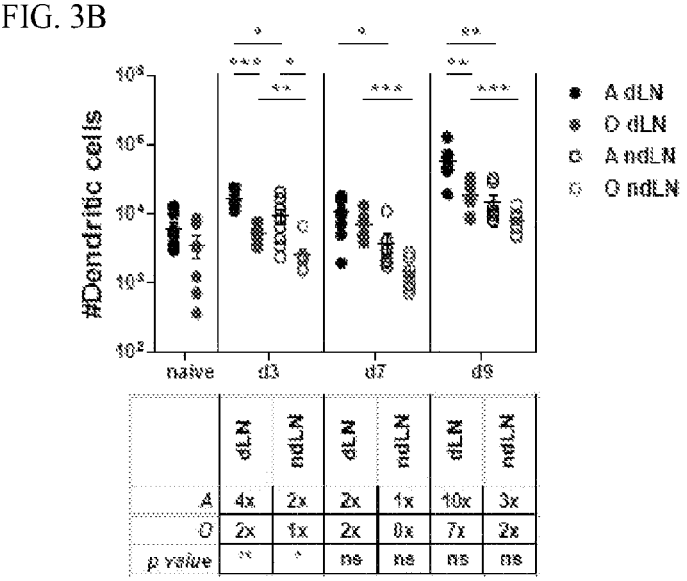
Figure 3C:
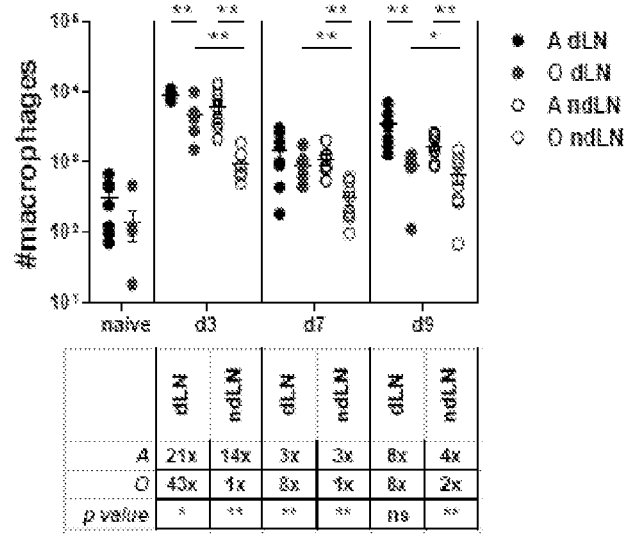
Figure 3D:
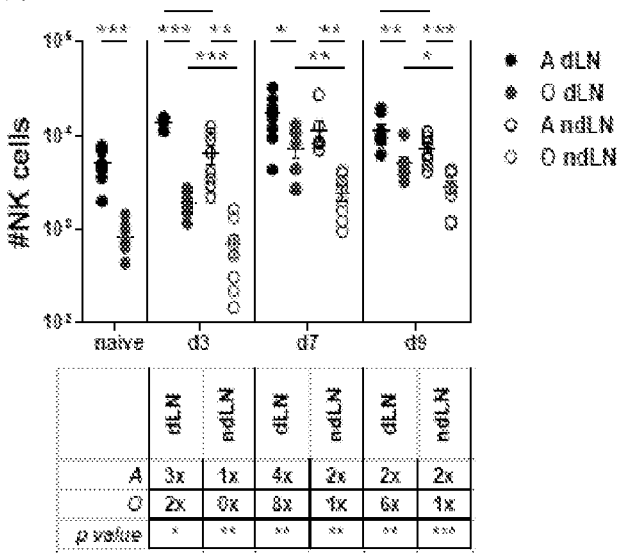

Dendritic cells (DCs), macrophages, and NK cells initiate the innate immune response sensing virus, potentiating early viral clearance, and producing cytokines. There is no deficiency in the number of CD11c$^+$ DCs or F4/80$^+$ macrophages in naïve LNs with age (FIG. 3B-C). However, O mice fail to accumulate the same number of DCs in either the dLN or ndLN on day 3 of CHIKV infection with the most dramatic fold-change over naïve at day 9 post-infection (FIG. 3B). In contrast to this, O mice have a dramatic 43-fold increase in the number of macrophages in the dLN on day 3 post-infection (FIG. 3C). Despite this seemingly robust response, they are unable to continue accumulation though day 9 when A mice again have more. While DCs and macrophages are comparable in naïve A and O LNs, NK cell numbers are decreased with age (FIG. 3D). Age-related defects in NK cell number and migration have been described as a key impairment leading to increased susceptibility to poxvirus infection (see, Fang, M., et al., 2010 The Journal of experimental medicine 207:2369-2381). Such data support that this defect is not virus-specific but rather a general age-associated defect that likely contributes to poor early viral clearance.

Figure 4:
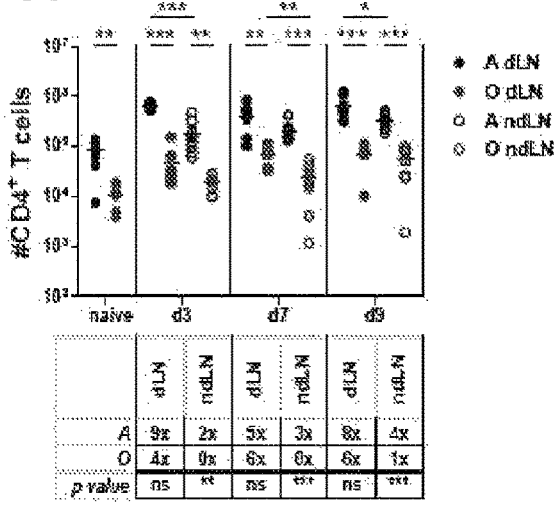
Figure 4:
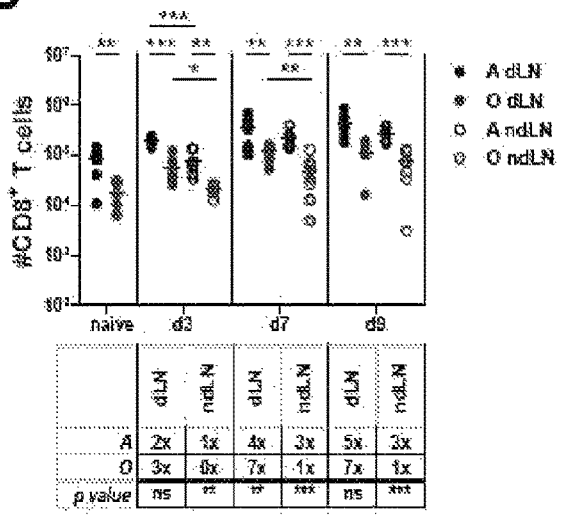
Figure 4:
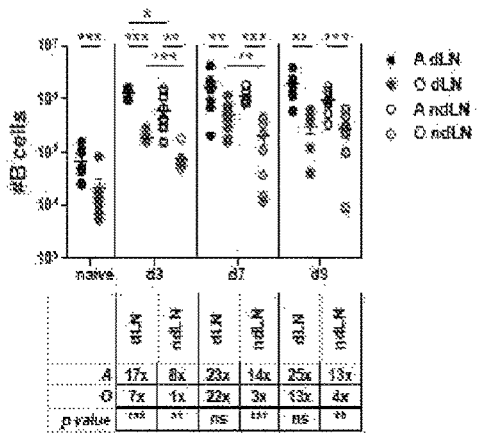
Figure 4:
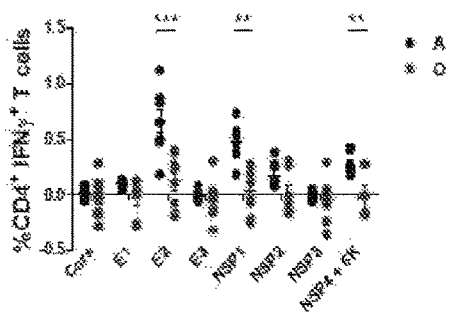
Figure 4:
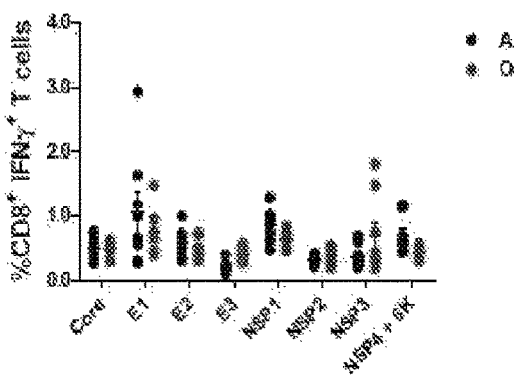

The adaptive immune response has been shown to play a role in both CHIKV-clearance and disease severity (see, Hawman, D. W., et al., 2013 Journal of virology 87:13878-13888; Teo, T. H., et al., 2013 Journal of immunology (Baltimore, Md.: 1950) 190:259-269). Specifically, WT C57BL/6 mice have increased joint pathology during the acute-phase of infection but eventually clear the virus and Rag–/– mice enjoy a seemingly mild to moderate acute-phase infection that never clears leading to a chronic arthralgia similar to what is experienced by some CHIKV patients. How these factors contribute to the measured age-related increased susceptibility is not so clear cut. There is a deficiency in the number of CD4 and CD8 T cells and B cells in the LN of naïve O mice and none of these populations are able to expand to equivalent numbers as compared to adult in the draining or non-draining LN (FIG. 4A-C). Further, the ndLN in O mice is practically uninvolved in the immune response with little to no increase in total numbers of cells (FIG. 4A-C) despite measured viral titers in non-inoculated control tissues on days 3 and 9 post-infection (FIG. 2B-C). Even at day 9, late in the acute disease period, the old LN has failed to catch up to A suggesting that the kinetics are not simply delayed but rather that the O LN cannot support the numbers of cells contained in an A LN. One possible explanation for this is that age-related degradation of LN stromal architecture leaves it incapable of supporting the same number and diversity of cell types measured in A. In fact, changes in stromal architecture of the LN with age have recently been discovered (C. D. Surh, personal communication; M. S. Diamond, personal communication) but will not be further discussed in this manuscript. The question then remained as to whether the infiltrating T cells are functionally competent. To test this splenocytes were isolated from O and A mice on day 7 post-infection and stimulated them with CHIKV peptide pools to evaluate the ability of CD4 and CD8 cells to produce IFNγ. Responses were detected against the same peptide pools in both A and O mice (FIG. 4D-E), suggesting that the CHIKV immunodominance profile does not change with age. CD4 T cell responses to CHIKV peptide stimulation revealed significantly lower frequency of IFNγ producing CD4 T cells directed against the E2, NSP1 and NSP4+6K regions of CHIKV (FIG. 4D). In contrast, no reproducible differences in the CD8 T cell response to CHIKV peptide stimulation with age was found (FIG. 4E). Such results may have been expected given that the clear immunodeficiency in O LN that CHIKV-swelling would be reduced in 0 mice similar to the reduced pathology in Rag–/– mice but this was not the case (FIG. 1). However, the delayed viral clearance and persistence at day 60 post-infection measured in 0 mice (FIG. 2A-D) does seemingly correlate with measurements in Rag–/– mice (see, Hawman, D. W., et al., 2013 Journal of virology 87:13878-13888).

Example IV

Figure 5:
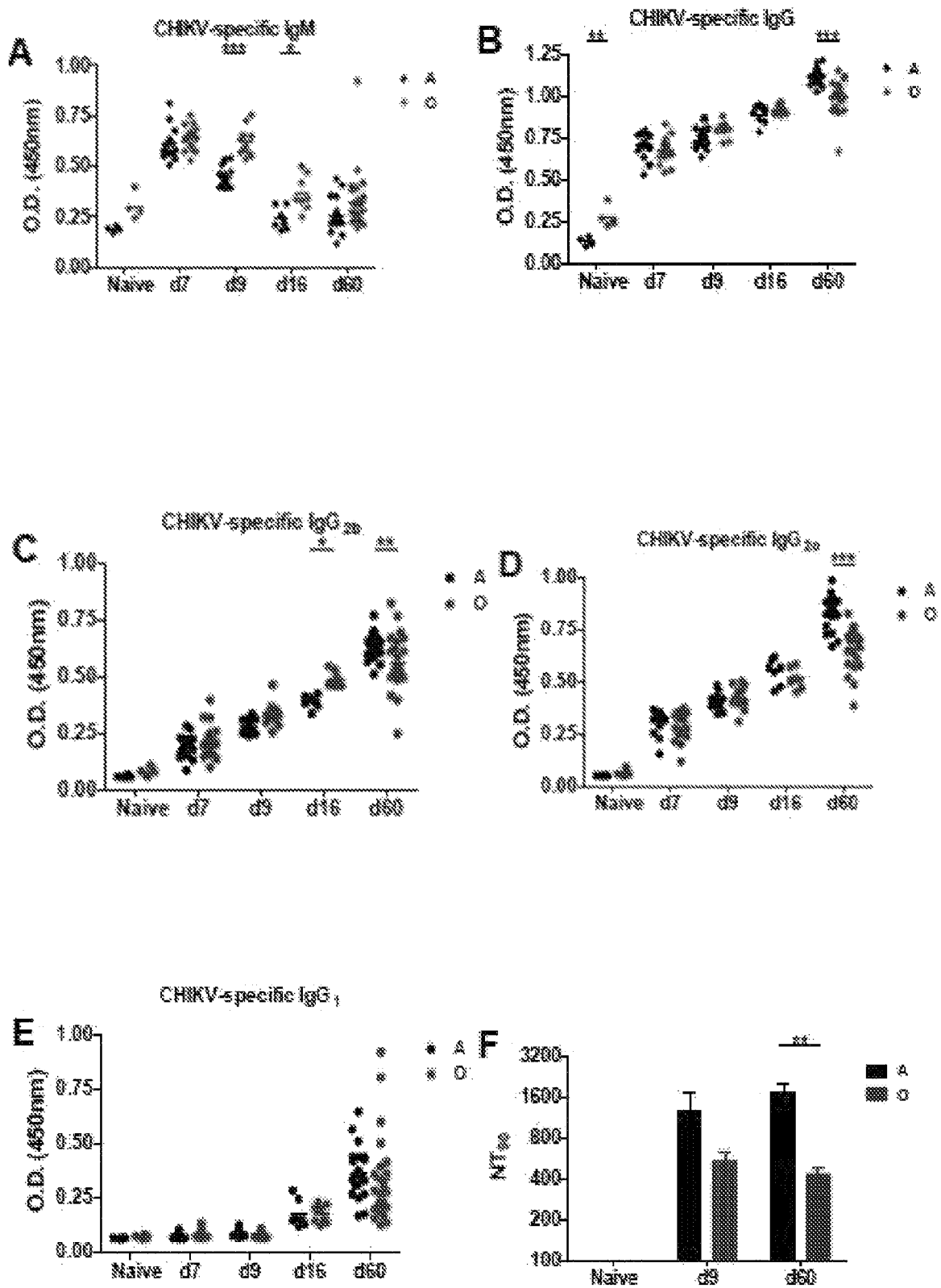

Anti-CHIKV Antibody Responses in O Mice are Poorly Neutralizing and Skewed in Isotype Experiments next assessed the B cell response to CHIKV in A and O mice by measuring the magnitude and isotype specificity of antibody production following infection. Anti-CHIKV antibodies were measured in naïve mice and on days 7, 9, 16, and 60 of CHIKV infection. Both A and O mice produce anti-CHIKV IgM antibody by d7 post-infection. In O mice, levels remain elevated over A through day 16 post-infection (FIG. 5A). This could result from delayed class switching in O mice, which has been described in the literature. CHIKV-specific total IgG antibody quantities were equal between O and A mice throughout acute infection but O mice have reduced amounts at day 60 post-infection (FIG. 5B). Isotype specificity of CHIKV Ab followed the same trend as total IgG over acute infection with equal amounts in A and O on days 7, 9, and 16 with one exception: anti-CHIKV IgG2b was elevated in O mice on d16. IgG2b isotype is associated with increased so-called "suppressive" cytokine production including TGF-β. By day 60 post-infection A mice expressed higher quantities of anti-CHIKV IgG2b and IgG2c, but not IgG1, isotype suggesting an ultimate failure for O mice to make robust antibody responses (FIG. 5C-E).

Finally, functional capacity of A and O serum to neutralize infectious virus was tested. Both A and O serum harvested on days 9 and 60 post-infection contained CHIKV neutralizing activity as compared to naïve serum (FIG. 5F). However, the neutralizing potency of O serum was inferior to A mice, and that difference was statistically significant on day 60 (FIG. 5F). Altogether these data suggest that the quantity and quality of antibodies produced in response to CHIKV infection in O mice is suboptimal, likely contributing to impaired clearance of the virus and failure to prevent arthritic disease. These observations closely parallel the results obtained in CD4–/– and IFNγ–/– mice (see, Lum, F. M., et al., 2013 Journal of immunology (Baltimore, Md.: 1950) 190:6295-6302), where impaired immunity to CHIKV has both cellular (CD4 cells) and humoral (Ab) components. It was therefore conclude that the CD4 lymphopenia measured in the LN (FIG. 4A) and decreased capacity of CHIKV-specific CD4 T cells to produce IFNγ (FIG. 4D) likely contribute to the total IgG and IgG2c antibody deficiency on day 60 post-infection.

Example V

Age-Related Dysbalance in Pro- and Anti-Inflammatory Mediators During CHIKV Infection Given the above age-related changes in Ab profiles responding to CHIKV and the profound defects in O mice mobilizing the adaptive immune response, evaluation of serum cytokine and chemokine profiles in A and O mice using Type I IFN ELISA's and a Luminex array was sought.

Figure 6:
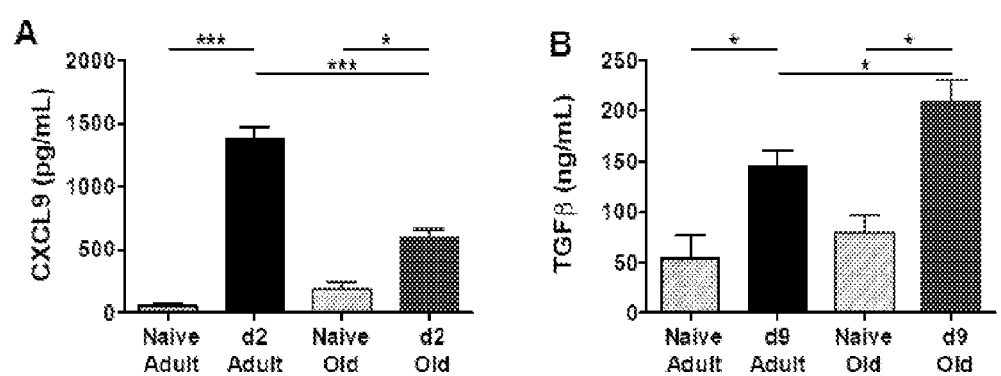

Such experiments failed to detect either Type I IFNα or β in the serum of infected A or O mice over days 1-4 post-infection. It is possible that even day 1 is too late, that the ELISA's used were not sensitive enough or that it would only be detected locally, an issue that remains unresolved in the present study. While most of the other cytokines and chemokines (by Luminex array) exhibited only minor differences between A and O mice (FIG. 9), significant differences in CXCL9 were detected. A dramatic increase in A and a significantly smaller increase in O serum CXCL9 concentration on day 2 post-CHIKV infection was found, which was confirmed by ELISA (FIGS. 6A and 9). CXCL9 is a proinflammatory chemokine that functions as a chemoattractant for activated lymphocytes. Moreover, O mice exhibited a significantly greater increase in TGF-β cytokine on day 9 post-CHIKV infection relative to A counterparts (FIG. 6B). Increased production of TGF-β in O mice during acute infection is not unique to CHIKV as this has been measured in a model of West Nile Virus infection (FIG. 10A) and TGF-β is a pleiotropic cytokine with diverse effects on the immune system that are incompletely understood. It is both made and utilized by almost all cells of the body and its tight regulation is considered critical for the mediation of proper immune responses. TGF-β can also be a switch-factor for murine antibody isotypes as well as for mediation of leukocyte recruitment and activation (see, McIntyre, T. M., et al., 1993 The Journal of experimental medicine 177:1031-1037; Wahl, S. M., et al., 1993 The Journal of experimental medicine 177:225-230). Indeed, 0 mice have increased CHIKV antibody of IgG2b isotype on d16 post-infection (FIG. 7C) supporting that the immune response in O mice is improperly coordinated through the action of TGF-β possibly contributing to increased disease severity measured in O mice.

Example VI

Blocking TGF-β in O Mice During Acute CHIKV-Infection Reduces Acute and Chronic Disease Severity and Restores Antibody Responses.

Figure 7:
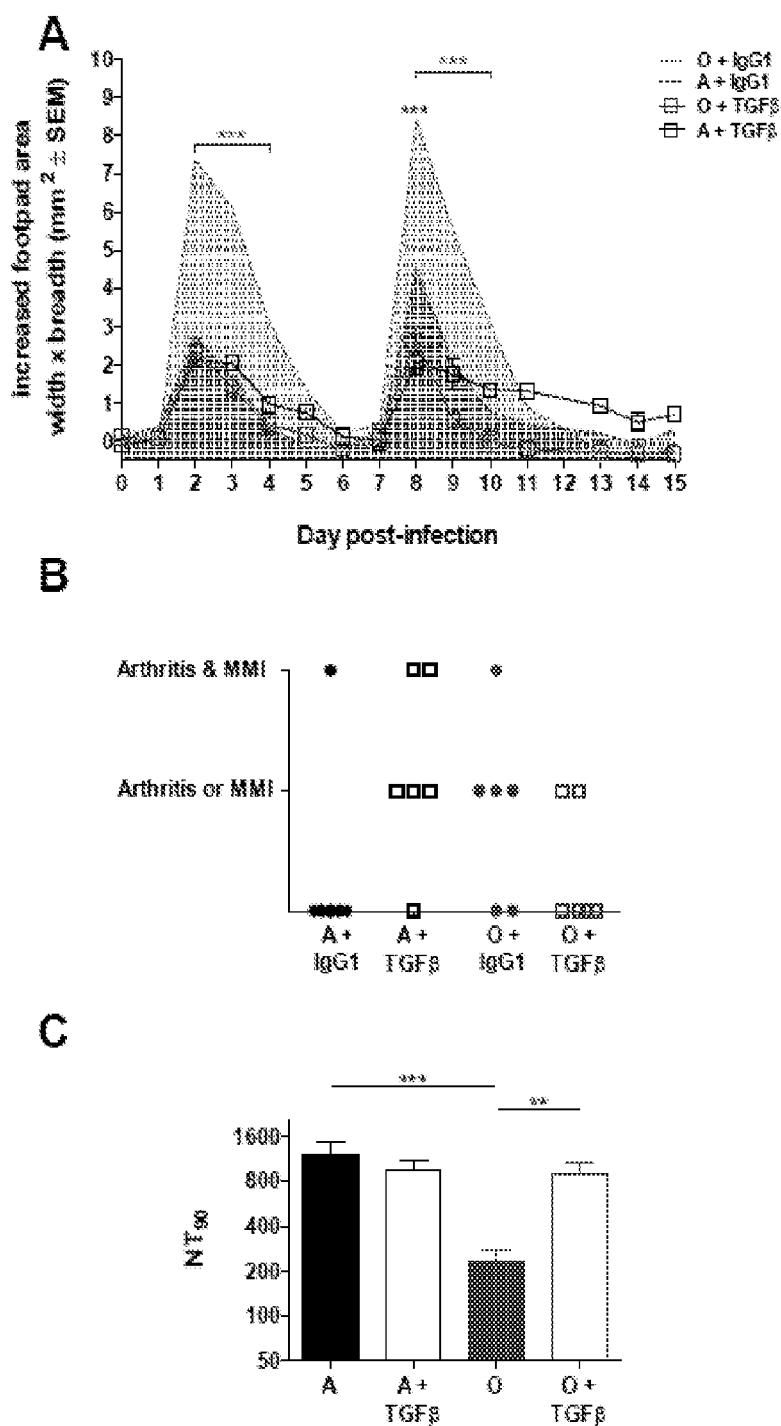

Our hypothesis was that elevated TGF-β production is a critical determinant in age-related increased disease severity and poor immune function. To test this A and O mice were treated with a local footpad injection of either anti-TGF-β antibody or isotype control on days −1, 1, 3 and 5 relative to CHIKV infection and confirmed a reduced concentration of TGF-β in serum with treatment (FIG. 10B). Footpad, but not intraperitoneal, injection of anti-TGF-β antibody effectively reduced both peaks of acute foot swelling in O mice (FIG. 7A) suggesting high levels of localized TGF-β contribute to the age-related increase in disease severity. TGF-β blockade in CHIKV infected A mice did not reduce disease severity during the early phase of swelling but did significantly reduce swelling during the late phase on day 8. This further supports the idea that a very intricate balance of pro- and anti-inflammatory cytokines and chemokines are required to coordinate an effective immune response to CHIKV and, perhaps even more importantly, directly influence disease pathogenesis. It should be noted that TGF-β treatment did not prevent swelling altogether, suggesting that there are other mediators of disease severity regardless of age. Further, there was no direct anti-viral effect of treatment measured as evidenced by viral titers in tissues on day 9 (FIG. 10C). At this point, the question remained as to whether blocking of TGF-β during acute infection would reduce chronic arthritis and/or restore immune functions related to optimal viral control. To determine this H&E stained tissue sections from anti-TGF-β or IgG1 antibody treated A and O mice at day 90 post-infection were evaluated for synovitis, arthritis, and metatarsal muscle inflammation using an established scoring system (see, Hawman, D. W., et al., 2013 Journal of virology 87:13878-13888). Such experiments revealed a similar incidence of synovitis for both infected and uninfected A and O mice possibly due to their ages at the time of harvest; 7 and 21-23 months, respectively. Additionally, and as was previously reported for Rag−/− and WT mice, there is very little pathology this far post-infection as compared to earlier stages of infection. However, it was detected that O mice treated with isotype control antibody have an increased incidence of chronic arthritis and/or metatarsal muscle inflammation (4 of 6 mice) as compared to A (1 of 6 mice) (FIG. 7B). This data taken with the increased viral copy data in FIG. 2D definitively show that O mice have an increased incidence of chronic CHIKV-disease. Further, this incidence is reduced by 50% when TGF-β is blocked during acute infection (FIG. 7B). Quite the opposite is the case for A mice where disease incidence is increased with TGF-β blockade (5 of 6 mice) (FIG. 7B). This increased incidence in A mice is unsurprising as TGF-β was expected to be tightly regulated in an intact and competent immune response. Disrupting this "optimum" balance should have potentially detrimental consequences. Experiments further evaluated the neutralizing capacity of antibody taken at this same time point during chronic disease and were able to determine that O mice treated with anti-TGF-β blockade during acute infection have restored capacity to neutralize CHIKV. Taken together, such results identify the action of TGF-β as a mechanism leading to age-related loss of immune system function and increased joint pathology in the course of CHIKV infection.

Example VII

Discussion.

In experiments conducted during the course of developing embodiments for the present invention, a mouse model was developed to evaluate the effect of age on disease and immunity to CHIKV. Disease in O animals followed the same course as in adults; however it resulted in prolonged viremia and more severe pathology. Importantly, it was shown that aged animals generate a quantitatively and qualitatively defective immune response at both innate and adaptive levels. Experiments demonstrated that a dysregulated TGF cytokine response is responsible for both the enhanced disease phenotype and a failure of the old immune system to mount an effective response. Such experiments indicate that this dysregulation is age-specific and is not playing a role in the disease measured in young animals.

The generation of an effective immune response against viruses requires the activation of early innate immune molecules that provide both a first line of a defense and important cues required to mediate an efficient and long lasting adaptive immune response. Even though the exact role of each arm of the immune response against CHIKV infection has not been completely elucidated, it is clear that both innate and adaptive components are required. Therefore, any age-related changes that occur at either of the two arms could profoundly affect the ability of the immune system to fight off the virus. Increased levels of pro-inflammatory cytokines (IFNαβ, IL-1β, IL-6, IL-12, IL-18, GMCSF, IFNγ, MCP-1 and CXCL9) measured early after CHIKV infection are key mediators regulating viral clearance. They also likely play a role in the recruitment of immune cells that contribute to the painful and debilitating arthritis characteristic to CHIKV infection. Evaluation of levels of pro-inflammatory cytokines in the serum of O and A mice on day 3 post infection did not reveal many age-related differences. The exception was in the levels of CXCL9, which were significantly lower in O serum. CXCL9 is a chemo-attractant, mostly secreted by macrophages, and responsible for the recruitment of lymphocytes. Its lower levels could potentially lead to reduced numbers of lymphocytes subsequently recruited to infected joints and draining lymph nodes. However, in addition to reduced recruitment of the O T and B lymphocytes to infected areas, the data also suggest that the differences in the numbers of lymphocytes detected in the dLN could be partially due to reduced lymphocyte numbers present in LN of naïve animals. Significantly smaller sizes of popliteal lymph nodes in O uninfected animals was observed, which during the course of the infection, were able to enlarge and expand their numbers. However, they never reached the degree of size or cellularity measured in the A counterparts. There could be multiple reasons for this, starting with a decline in naïve T cells with aging (see, Decman, V., et al., 2012 Journal of immunology (Baltimore, Md.: 1950) 188:1933-1941; Rudd, B. D., et al., 2011 Proceedings of the National Academy of Sciences of the United States of America 108:13694-13699). This could be due to the age-related changes in the architecture and stromal components of the lymph nodes that affect availability of T cell homeostatic cytokines (Becklund et al., submitted). Data are also consistent with important age related differences in cells homing to inflamed LN under the conditions of infection.

In addition to decreased quantity of the T cell response, CHIKV peptide stimulation revealed reduced ability of old CD4 T cells to produce IFNγ in response to viral epitopes. Altogether, these data suggest that prolonged clinical pathology observed at the site of viral infection in O mice is probably not mediated by CD4 or CD8 T cells, as their numbers and function are decreased and not increased in aging. Consistent with that, similar initial viral titers were found but an age-related delay in clearance. Viral loads in the local foot/ankle tissue were much higher in O mice compared to A on day 3 and remained at detectable levels on day 9 possibly contributing to the increased swelling measured in the O mice.

Of major importance is another observation showing the differences in cytokine levels with potential link to the development of a subsequently dysregulated adaptive response. As previously reported, CHIKV infection induces strongly neutralizing IgM (early) and IgG2c (memory phase) antibodies, which have been shown to play an important role in the clearance of the infection. The data revealed that in addition to overall lower levels of anti-CHIKV specific Abs with poor neutralizing capacity, O mice also produced Abs with skewed isotype. IgM isotype antibodies in O mice were produced longer at the expense of poor conversion to different IgG isotypes. Even more interestingly, O mice exhibited higher early titers of IgG2b possibly owing to a skewed cytokine milieu in the draining LN. Similar phenomenon of reduced conversion into IgG2b has been previously described to be associated with suppressive environment, which generates Th17 responses. Concomitant with this observation increased levels of serum TGF-β levels were found, and it was shown that higher TGF-β levels in the O mice led not only to increased conversion into IgG2b isotype but also established an environment conducive to swelling and tissue pathogenesis. Because TGF-β blocking reversed all the above phenomena, such data suggest that with aging, increased TGF-β levels tipped the balance away from generation of an efficient and protective immune response leading to chronic arthritis.

Altogether this study identifies different aspects of dysfunctional immune response against CHIKV infection in O mice. Age related alterations are described at both innate and adaptive levels, which individually and synergistically contribute to increased susceptibility to CHIKV infection and CHIKV induced pathology in the elderly. Furthermore, such results identify a potential target for immune intervention to remedy the pathology associated with CHIKV infection in cases when TGF-β levels during acute infection are elevated.

Example VIII

This example describes the materials and methods for Examples I-VII.
Materials and Methods
Mice O (18 months) C57BL/6 (B6) mice were purchased from the National Institute on Aging, and A (12 weeks) B6 mice were purchased from The Jackson Laboratory. Mice were maintained and experiments conducted under guidelines and approval of the Institutional Animal Care and Use Committee of the University of Arizona. All CHIKV experiments were conducted within U.S. Department of Agriculture-inspected biosafety level 3 facilities.

Virus and Titer

CHIKV strain SL15649 (Genbank accession no. GU189061) was isolated from a serum sample collected from a febrile patient in Sri Lanka in 2006. It was propagated twice in Vero cells before the generation of an infectious cDNA clone (see, Morrison, T. E., et al., 2011 The American journal of pathology 178:32-40). Virus for use in experiments was propagated and purified as previously described (see, Silva, L. A., S. Khomandiak, A. W. Ashbrook, R. Weller, M. T. Heise, T. E. Morrison, and T. S. Dermody. 2013. A Single Amino-Acid Polymorphism in Chikungunya Virus E2 Glycoprotein Influences Glycosaminoglycan Utilization. Journal of virology). Virus titer was determined by plaque assay on Vero cells (see, Morrison, T. E., et al., 2011 The American journal of pathology 178:32-40).

Animal Infection and Evaluation of Disease

Mice were anesthetized with isoflurane and infected via subcutaneous footpad (f.p.) route with 1000 pfu of CHIKV in 10 uL sterile saline. Foot swelling was measured daily with calipers from 0 to 21 days post-infection. Footpad area was determined as (height×width) and expressed as increased footpad area over the day 0 measurement.

Viral Quantification

Viral loads in serum and tissue were done by standard plaque assay on Vero cells. Tissues were disrupted in a mini-beadbeater-96 (BioSpec Products, Bartlesville, Okla.) with 1 mm glass beads in a 2 mL tube with 5% FBS DMEM before and after being stored at −80° C.

Flow Cytometry and Intracellular Staining

Popliteal lymph nodes were treated with accutase (eBioscience, San Diego, Calif.) for 30 min at 37° C. and then disassociated over a 40 uM cell strainer. Cells from lymph node were Fc blocked for 30 min, incubated overnight in a saturating dose of surface antibodies against CD3, CD4, CD8a, CD19, CD11b, CD11c, NK1.1 and F4/80 (Ebioscience, San Diego, Calif.) and then stained for viability with Live/Dead Yellow (Life Technologies, Grand Island, N.Y.). Spleen was disassociated over a 40 uM cell strainer. Overlapping peptide pools from each of the nine CHIKV proteins were added to 2×10$^6$ splenocytes in the presence of 5 μg/ml brefeldin A (BFA; Sigma-Aldrich, St. Louis, Mo.) for 6 h at 37° C. The cells were then incubated overnight in a saturating dose of surface antibodies against CD3, CD4, CD8a. After being washed, the cells were fixed and permeabilized with Foxp3/Transcription Factor Staining Buffer Set and intracellular IFN-γ antibody was added for 30 min. Samples were acquired using a BD LSR Fortessa cytometer (BD Bioscience, San Jose, Calif.) and analyzed by FlowJo software (Tree Star, Ashland, Oreg.). Cell counts extrapolated from either a hand count on a hemacytometer or by CBC differential collected on a Hemavet LV (Drew Scientific, Waterbury, Conn.). These two methods of counting were confirmed to be consistent.

Antibody Quantification and Isotyping

Antibody titers were assessed by CHIKV infectious cell lysate based enzyme-linked immunosorbent assay (ELISA). CHIKV-infected lysate was generated by infection of primary human fibroblasts harvested at 48 hours post-infection. Cells were dounce homogenized 30 strokes and stored at −80° C. 96 well Immulon 2 HB plates (Thermo Labsystems, Franklin, Mass.) were coated with 50 uL of CHIKV-infected or control uninfected lysate diluted 1:200 in carbonate buffer overnight at 4° C. Plates were blocked with PBS-0.05% Tween-20+5% dry nonfat milk for 30 min at room temperature with shaking. Serum was diluted 1:50 in PBS-0.05% Tween-20+5% dry nonfat milk and incubated for 1 hour at room temperature with shaking. Horseradish peroxidase-labeled goat anti-mouse IgG (KPL, Gaithersburg, Md.), IgM, IgG1, IgG2b, IgG2c (Southern Biotech, Birmingham, Ala.) antibodies were used for detection. Reactions were developed with 3,3',5,5'-Tetramethylbenzidine dihydrochloride (Sigma-Aldrich, St. Louis, Mo.) and terminated with 1M H2SO4. Absorbance was measured at 450 nm.

Neutralization Assay

Two-fold dilutions of heat-inactivated mouse serum were incubated with CHIKV for 2.5 hours at 37° C. Serum-virus complexes were added to Vero cells in 96 well plates. After 2 hours, cells were overlaid with 1% (w/v) methylcellulose in Modified Eagle Media (MEM) supplemented with 5% FBS. Plates were developed with 0.5% (w/v) crystal violet 48 hours later. Neutralization titers were determined as the well with a 90% reduction in plaques ($NT_{90}$) after comparison to wells infected with CHIKV in the absence of serum.

Serum Cytokine Assays

MIG/CXCL9 (R&D Systems Inc, Minneapolis, Minn.) and TGF-β (eBioscience, San Diego, Calif.) ELISAs were performed following manufacturer instructions.

TGF-β Blockade 100 ug of TGF-β antibody clone 1D11.16.8 (Bio X Cell, West Lebanon, N.H.) or IgG1 isotype control (clone MOPC-21) in 20 uL sterile saline was injected via f.p. route on days −1, 1, 3, and 5 of CHIKV infection.

Histology

Mice were euthanized by isoflurane overdose and foot and ankle tissues were collected then fixed in 10% neutral buffered formalin for 24 hours. Fixed tissues were decalcified, embedded in paraffin wax, processed to obtain 5-pin sections, and stained with Hematoxylin and Eosin per established protocols.

Statistical Analysis

Data were analyzed using Prism Graph Pad software and the statistical test referenced in each figure.

Example IX

This example shows TGF-β levels in human beings suffering from CHIKV (see, FIG. 8). There is no difference between young and aged humans for TGF-β levels. A significant spike in active TGF-β levels during acute CHIKV infection as compared to uninfected plasma samples.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A method of treating Chikungunya virus infection in a subject, comprising administering to the subject an effective amount of an anti-TGF-β antibody that inhibits TGF-β1, TGF-β2, and/or TGF-β3 activity, wherein said antibody is TGF-β antibody clone 1D11.16.8, and wherein the treating results in a decrease in one or more symptoms related to the Chikungunya virus infection.

2. The method of claim 1, further comprising administering to the subject an effective amount of at least one additional therapeutic agent.

3. The method of claim 2, wherein the at least one additional therapeutic agent reduces alphaviral replication, reduces the time to alphaviral clearance, reduces morbidity or mortality in the clinical course of the alphaviral infection, reduces subject symptoms caused by the alphaviral infection, or reduces a side effect of the agent that inhibits TGF-β activity.

4. The method of claim 2, wherein the anti-TGF-β antibody and at least one additional therapeutic agent are administered together as part of a single composition or wherein the TGF-β inhibitor and at least one additional therapeutic agent are administered separately.

5. The method of claim 1, wherein the subject is a human.

6. The method of claim 1, wherein the one or more symptoms related to the Chikungunya virus infection are selected from the group consisting of encephalitis, arthritis, rashes, fevers, headache, nausea, myalgia, arthralgia, arthropathy, chills, diarrhea, vomiting, lymphadenitis, malaise, and muscle soreness.

* * * * *